United States Patent [19]
Ohto et al.

[11] Patent Number: 5,882,909
[45] Date of Patent: Mar. 16, 1999

[54] NUCLEIC ACID ENCODING MUTANT GERANYLGERANYL DIPHOSPHATE SYNTHASE

[75] Inventors: Chikara Ohto; Chika Asada, both of Toyota; Shinichi Ohnuma, Sendai; Tokuzo Nishino, Sendai; Kazutake Hirooka, Sendai; Hisashi Hemmi, Sendai, all of Japan

[73] Assignee: Toyota Jidosha Kabushiki Kaisha, Toyota, Japan

[21] Appl. No.: 52,962

[22] Filed: Apr. 1, 1998

Related U.S. Application Data

[62] Division of Ser. No. 705,377, Aug. 29, 1996, Pat. No. 5,807,725.

[30] Foreign Application Priority Data

Sep. 1, 1995 [JP] Japan ................................ 7-247043

[51] Int. Cl.$^6$ .............. C12N 6/10; C12N 1/20; C12N 15/00; C07H 21/04
[52] U.S. Cl. ............... 435/193; 435/252.3; 435/320.1; 536/23.2
[58] Field of Search ................ 435/193, 252.3, 435/320.1; 536/23.2

[56] References Cited

FOREIGN PATENT DOCUMENTS 0 674 000 A2  9/1995  European Pat. Off. .

OTHER PUBLICATIONS

Brems, et al., *Biochemistry*, 20:13, pp. 3711–3718, 1981.
Joly et akl., *J. Bio. Chem.*, 268:36, pp. 26983–26989, Dec. 25 1993.
Chen, et al., *Protein Science*, vol. 3, pp. 600–607, 1994.
Song, et al., *Proc. Natl. Acad. Sci. USA*, vol. 91, pp. 3044–3048, Apr. 1994.
Koyama, et al., *Biochemistry*, 33:42, pp. 12644–12648, 1994.
Ohnuma, et al., *J. Biol. Chem.*, 271:18831–18837, 1996.
Math, et al., *Proc. Natl. Acad. Sci. USA*, 89:6761–6764, Aug. 1992.
Ohnuma, et al., *J. Biol. Chem.*, 269:20, pp. 14792–14797, May 20 1994.
P.F. Marrero et al., *J. Biol. Chem.*, 267:30, pp. 21873–21878, 1992.
Ohnuma et al. (Apr. 26, 1996) J. Biol. Chem. 271, pp. 10087–10095.

*Primary Examiner*—Robert A. Wax
*Assistant Examiner*—Elizabeth Slobodyansky
*Attorney, Agent, or Firm*—Kenyon & Kenyon

[57] ABSTRACT

The present invention discloses a mutated enzyme comprising a geranylgeranil diphosphate synthase having its origin in wild type *Sulfolobus acidocaldarius* wherein, at least one of phenylalanine at position 77, methionine at position 85, valine at position 99, tyrosine at position 101, phenylalanine at position 118, arginine at position 199 and aspartic acid at position 312 is substituted with another amino acid.

5 Claims, 5 Drawing Sheets

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH:993
        ( B ) TYPE:Nucleic acid
        ( C ) STRANDEDNESS:Double
        ( D ) TOPOLOGY:Linear ( i i ) MOLECULE TYPE:Genomic DNA ( v i ) ORIGINAL SOURCE:
        ( A ) ORGANISM:Sulfolobus acidocaldarius ( x i ) SEQUENCE DESCRIPTION: SEQ ID NO:1:

```
ATG  AGT  TAC  TTT  GAC  AAC  TAT  TTT  AAT  GAG  ATT  GTT  AAT  TCT  GTA  AAC        48
Met  Ser  Tyr  Phe  Asp  Asn  Tyr  Phe  Asn  Glu  Ile  Val  Asn  Ser  Val  Asn
                    5                        10                       15

GAC  ATT  ATT  AAG  AGC  TAT  ATA  TCT  GGA  GAT  GTT  CCT  AAA  CTA  TAT  GAA        96
Asp  Ile  Ile  Lys  Ser  Tyr  Ile  Ser  Gly  Asp  Val  Pro  Lys  Leu  Tyr  Glu
               20                        25                       30

GCC  TCA  TAT  CAT  TTG  TTT  ACA  TCT  GGA  GGT  AAG  AGG  TTA  AGA  CCA  TTA       144
Ala  Ser  Tyr  His  Leu  Phe  Thr  Ser  Gly  Gly  Lys  Arg  Leu  Arg  Pro  Leu
          35                        40                        45

ATC  TTA  ACT  ATA  TCA  TCA  GAT  TTA  TTC  GGA  GGA  CAG  AGA  GAA  AGA  GCT       192
Ile  Leu  Thr  Ile  Ser  Ser  Asp  Leu  Phe  Gly  Gly  Gln  Arg  Glu  Arg  Ala
     50                        55                        60

TAT  TAT  GCA  GGT  GCA  GCT  ATT  GAA  GTT  CTT  CAT  ACT  TTT  ACG  CTT  GTG       240
Tyr  Tyr  Ala  Gly  Ala  Ala  Ile  Glu  Val  Leu  His  Thr  Phe  Thr  Leu  Val
65                       70                        75                       80

CAT  GAT  GAT  ATT  ATG  GAT  CAA  GAT  AAT  ATC  AGA  AGA  GGG  TTA  CCC  ACA       288
His  Asp  Asp  Ile  Met  Asp  Gln  Asp  Asn  Ile  Arg  Arg  Gly  Leu  Pro  Thr
               85                        90                       95
```

```
GTC  CAC  GTG  AAA  TAC  GGC  TTA  CCC  TTA  GCA  ATA  TTA  GCT  GGG  GAT  TTA     336
Val  His  Val  Lys  Tyr  Gly  Leu  Pro  Leu  Ala  Ile  Leu  Ala  Gly  Asp  Leu
               100                 105                      110

CTA  CAT  GCA  AAG  GCT  TTT  CAG  CTC  TTA  ACC  CAG  GCT  CTT  AGA  GGT  TTG     384
Leu  His  Ala  Lys  Ala  Phe  Gln  Leu  Leu  Thr  Gln  Ala  Leu  Arg  Gly  Leu
          115                      120                      125

CCA  AGT  GAA  ACC  ATA  ATT  AAG  GCT  TTC  GAT  ATT  TTC  ACT  CGT  TCA  ATA     432
Pro  Ser  Glu  Thr  Ile  Ile  Lys  Ala  Phe  Asp  Ile  Phe  Thr  Arg  Ser  Ile
     130                      135                           140

ATA  ATT  ATA  TCC  GAA  GGA  CAG  GCA  GTA  GAT  ATG  GAA  TTT  GAG  GAC  AGA     480
Ile  Ile  Ile  Ser  Glu  Gly  Gln  Ala  Val  Asp  Met  Glu  Phe  Glu  Asp  Arg
145                           150                 155                      160

ATT  GAT  ATA  AAG  GAG  CAG  GAA  TAC  CTT  GAC  ATG  ATC  TCA  CGT  AAG  ACA     528
Ile  Asp  Ile  Lys  Glu  Gln  Glu  Tyr  Leu  Asp  Met  Ile  Ser  Arg  Lys  Thr
                    165                      170                      175

GCT  GCA  TTA  TTC  TCG  GCA  TCC  TCA  AGT  ATA  GGC  GCA  CTT  ATT  GCT  GGT     576
Ala  Ala  Leu  Phe  Ser  Ala  Ser  Ser  Ser  Ile  Gly  Ala  Leu  Ile  Ala  Gly
               180                           185                 190

GCT  AAT  GAT  AAT  GAT  GTA  AGA  CTG  ATG  TCT  GAT  TTC  GGT  ACG  AAT  CTA     624
Ala  Asn  Asp  Asn  Asp  Val  Arg  Leu  Met  Ser  Asp  Phe  Gly  Thr  Asn  Leu
          195                      200                      205

GGT  ATT  GCA  TTT  CAG  ATT  GTT  GAC  GAT  ATC  TTA  GGT  CTA  ACA  GCA  GAC     672
Gly  Ile  Ala  Phe  Gln  Ile  Val  Asp  Asp  Ile  Leu  Gly  Leu  Thr  Ala  Asp
     210                      215                           220

GAA  AAG  GAA  CTT  GGA  AAG  CCT  GTT  TTT  AGT  GAT  ATT  AGG  GAG  GGT  AAA     720
Glu  Lys  Glu  Leu  Gly  Lys  Pro  Val  Phe  Ser  Asp  Ile  Arg  Glu  Gly  Lys
225                           230                 235                      240

AAG  ACT  ATA  CTT  GTA  ATA  AAA  ACA  CTG  GAG  CTT  TGT  AAA  GAG  GAC  GAG     768
Lys  Thr  Ile  Leu  Val  Ile  Lys  Thr  Leu  Glu  Leu  Cys  Lys  Glu  Asp  Glu
                    245                      250                      255

AAG  AAG  ATT  GTC  CTA  AAG  GCG  TTA  GGT  AAT  AAG  TCA  GCC  TCA  AAA  GAA     816
Lys  Lys  Ile  Val  Leu  Lys  Ala  Leu  Gly  Asn  Lys  Ser  Ala  Ser  Lys  Glu
               260                      265                      270

GAA  TTA  ATG  AGC  TCA  GCA  GAT  ATA  ATT  AAG  AAA  TAC  TCT  TTA  GAT  TAT     864
Glu  Leu  Met  Ser  Ser  Ala  Asp  Ile  Ile  Lys  Lys  Tyr  Ser  Leu  Asp  Tyr
          275                      280                      285

GCA  TAC  AAT  TTA  GCA  GAG  AAA  TAT  TAT  AAA  AAT  GCT  ATA  GAC  TCT  TTA     912
Ala  Tyr  Asn  Leu  Ala  Glu  Lys  Tyr  Tyr  Lys  Asn  Ala  Ile  Asp  Ser  Leu
     290                      295                           300

AAT  CAA  GTC  TCC  TCT  AAG  AGT  GAT  ATA  CCT  GGA  AAG  GCT  TTA  AAA  TAT     960
Asn  Gln  Val  Ser  Ser  Lys  Ser  Asp  Ile  Pro  Gly  Lys  Ala  Leu  Lys  Tyr
305                           310                 315                      320

CTA  GCT  GAA  TTT  ACG  ATA  AGA  AGG  AGA  AAA  TAA                               993
Leu  Ala  Glu  Phe  Thr  Ile  Arg  Arg  Arg  Lys
               325                      330
```

( 2 ) INFORMATION FOR SEQ ID NO:2:

( i ) SEQUENCE CHARACTERISTICS:
        ( A ) LENGTH:993
        ( B ) TYPE:Nucleic acid
        ( C ) STRANDEDNESS:Double
        ( D ) TOPOLOGY:Linear ( i i ) MOLECULE TYPE:Mutated genomic DNA ( x i ) SEQUENCE DESCRIPTION:SEQ ID NO:2:

```
ATG  AGT  TAC  TTT  GAC  AAC  TAT  TTT  AAT  GAG  ATT  GTT  AAT  TCT  GTA  AAC      48
Met  Ser  Tyr  Phe  Asp  Asn  Tyr  Phe  Asn  Glu  Ile  Val  Asn  Ser  Val  Asn
                    5                        10                      15

GAC  ATT  ATT  AAG  AGC  TAT  ATA  TCT  GGA  GAT  GTT  CCT  AAA  CTA  TAT  GAA      96
Asp  Ile  Ile  Lys  Ser  Tyr  Ile  Ser  Gly  Asp  Val  Pro  Lys  Leu  Tyr  Glu
               20                       25                      30
```

```
GCC TCA TAT CAT TTG TTT ACA TCT GGA GGT AAG AGG TTA AGA CCA TTA        144
Ala Ser Tyr His Leu Phe Thr Ser Gly Gly Lys Arg Leu Arg Pro Leu
    35                      40                  45

ATC TTA ACT ATA TCA TCA GAT TTA TTC GGA GGA CAG AGA GAA AGA GCT        192
Ile Leu Thr Ile Ser Ser Asp Leu Phe Gly Gly Gln Arg Glu Arg Ala
    50                      55                  60

TAT TAT GCA GGT GCA GCT ATT GAA GTT CTT CAT ACT TTT ACG CTT GTG        240
Tyr Tyr Ala Gly Ala Ala Ile Glu Val Leu His Thr Phe Thr Leu Val
65                       70                  75                  80

CAT GAT GAT ATT ATA GAT CAA GAT AAT ATC AGA AGA GGG TTA CCC ACA        288
His Asp Asp Ile Ile Asp Gln Asp Asn Ile Arg Arg Gly Leu Pro Thr
            85                      90                  95

GTC CAC GTG AAA TAC GGC TTA CCC TTA GCA ATA TTA GCT GGG GAT TTA        336
Val His Val Lys Tyr Gly Leu Pro Leu Ala Ile Leu Ala Gly Asp Leu
            100                     105                 110

CTA CAT GCA AAG GCT TTT CAG CTC TTA ACC CAG GCT CTT AGA GGT TTG        384
Leu His Ala Lys Ala Phe Gln Leu Leu Thr Gln Ala Leu Arg Gly Leu
        115                     120                 125

CCA AGT GAA ACC ATA ATT AAG GCT TTC GAT ATT TTC ACT CGT TCA ATA        432
Pro Ser Glu Thr Ile Ile Lys Ala Phe Asp Ile Phe Thr Arg Ser Ile
    130                     135                 140

ATA ATT ATA TCC GAA GGA CAG GCA GTA GAT ATG GAA TTT GAG GAC AGA        480
Ile Ile Ile Ser Glu Gly Gln Ala Val Asp Met Glu Phe Glu Asp Arg
145                     150                 155                 160

ATT GAT ATA AAG GAG CAG GAA TAC CTT GAC ATG ATC TCA CGT AAG ACA        528
Ile Asp Ile Lys Glu Gln Glu Tyr Leu Asp Met Ile Ser Arg Lys Thr
            165                     170                 175

GCT GCA TTA TTC TCG GCA TCC TCA AGT ATA GGC GCA CTT ATT GCT GGT        576
Ala Ala Leu Phe Ser Ala Ser Ser Ser Ile Gly Ala Leu Ile Ala Gly
                180                     185                 190

GCT AAT GAT AAT GAT GTA AAA CTG ATG TCT GAT TTC GGT ACG AAT CTA        624
Ala Asn Asp Asn Asp Val Lys Leu Met Ser Asp Phe Gly Thr Asn Leu
            195                     200                 205

GGT ATT GCA TTT CAG ATT GTT GAC GAT ATC TTA GGT CTA ACA GCA GAC        672
Gly Ile Ala Phe Gln Ile Val Asp Asp Ile Leu Gly Leu Thr Ala Asp
        210                     215                 220

GAA AAG GAA CTT GGA AAG CCT GTT TTT AGT GAT ATT AGG GAG GGT AAA        720
Glu Lys Glu Leu Gly Lys Pro Val Phe Ser Asp Ile Arg Glu Gly Lys
225                     230                 235                 240

AAG ACT ATA CTT GTA ATA AAA ACA CTG GAG CTT TGT AAA GAG GAC GAG        768
Lys Thr Ile Leu Val Ile Lys Thr Leu Glu Leu Cys Lys Glu Asp Glu
            245                     250                 255

AAG AAG ATT GTC CTA AAG GCG TTA GGT AAT AAG TCA GCC TCA AAA GAA        816
Lys Lys Ile Val Leu Lys Ala Leu Gly Asn Lys Ser Ala Ser Lys Glu
            260                     265                 270

GAA TTA ATG AGC TCA GCA GAT ATA ATT AAG AAA TAC TCT TTA GAT TAT        864
Glu Leu Met Ser Ser Ala Asp Ile Ile Lys Lys Tyr Ser Leu Asp Tyr
        275                     280                 285

GCA TAC AAT TTA GCA GAG AAA TAT TAT AAA AAT GCT ATA GAC TCT TTA        912
Ala Tyr Asn Leu Ala Glu Lys Tyr Tyr Lys Asn Ala Ile Asp Ser Leu
    290                     295                 300

AAT CAA GTC TCC TCT AAG AGT AAT ATA CCT GGA AAG GCT TTA AAA TAT        960
Asn Gln Val Ser Ser Lys Ser Asn Ile Pro Gly Lys Ala Leu Lys Tyr
305                     310                 315                 320

CTA GCT GAA TTT ACG ATA AGA AGG AGA AAA TAA                            993
Leu Ala Glu Phe Thr Ile Arg Arg Arg Lys
                325                     330
```

( 2 ) INFORMATION FOR SEQ ID NO:3:

(i) SEQUENCE CHARACTERISTICS:
    (A) LENGTH:993
    (B) TYPE:Nucleic acid
    (C) STRANDEDNESS:Double strand
    (D) TOPOLOGY:Linear (ii) MOLECULE TYPE: Mutated genomic DNA (xi) SEQUENCE DESCRIPTION: SEQ ID NO:3:

| ATG | AGT | TAC | TTT | GAC | AAC | TAT | TTT | AAT | GAG | ATT | GTT | AAT | TCT | GTA | AAC | 48 |
| Met | Ser | Tyr | Phe | Asp | Asn | Tyr | Phe | Asn | Glu | Ile | Val | Asn | Ser | Val | Asn | |
| | | | | 5 | | | | | 10 | | | | | 15 | | |

| GAC | ATT | ATT | AAG | AGC | TAT | ATA | TCT | GGA | GAT | GTT | CCT | AAA | CTA | TAT | GAA | 96 |
| Asp | Ile | Ile | Lys | Ser | Tyr | Ile | Ser | Gly | Asp | Val | Pro | Lys | Leu | Tyr | Glu | |
| | | | 20 | | | | | 25 | | | | | 30 | | | |

| GCC | TCA | TAT | CAT | TTG | TTT | ACA | TCT | GGA | GGT | AAG | AGG | TTA | AGA | CCA | TTA | 144 |
| Ala | Ser | Tyr | His | Leu | Phe | Thr | Ser | Gly | Gly | Lys | Arg | Leu | Arg | Pro | Leu | |
| | | | 35 | | | | 40 | | | | | 45 | | | | |

| ATC | TTA | ACT | ATA | TCA | TCA | GAT | TTA | TTC | GGA | GGA | CAG | AGA | GAA | AGA | GCT | 192 |
| Ile | Leu | Thr | Ile | Ser | Ser | Asp | Leu | Phe | Gly | Gly | Gln | Arg | Glu | Arg | Ala | |
| | | 50 | | | | 55 | | | | | 60 | | | | | |

| TAT | TAT | GCA | GGT | GCA | GCT | ATT | GAA | GTT | CTT | CAT | ACT | TTT | ACG | CTT | GTG | 240 |
| Tyr | Tyr | Ala | Gly | Ala | Ala | Ile | Glu | Val | Leu | His | Thr | Phe | Thr | Leu | Val | |
| 65 | | | | | 70 | | | | | 75 | | | | | 80 | |

| CAT | GAT | GAT | ATT | ATG | GAT | CAA | GAT | AAT | ATC | AGA | AGA | GGG | TTA | CCC | ACA | 288 |
| His | Asp | Asp | Ile | Met | Asp | Gln | Asp | Asn | Ile | Arg | Arg | Gly | Leu | Pro | Thr | |
| | | | | 85 | | | | | 90 | | | | | 95 | | |

| GTC | CAC | GTG | AAA | TAC | GGC | TTA | CCC | TTA | GCA | ATA | TTA | GCT | GGG | GAT | TTA | 336 |
| Val | His | Val | Lys | Tyr | Gly | Leu | Pro | Leu | Ala | Ile | Leu | Ala | Gly | Asp | Leu | |
| | | | 100 | | | | | 105 | | | | | 110 | | | |

| CTA | CAT | GCA | AAG | GCT | CTT | CAG | CTC | TTA | ACC | CAG | GCT | CTT | AGA | GGT | TTG | 384 |
| Leu | His | Ala | Lys | Ala | Leu | Gln | Leu | Leu | Thr | Gln | Ala | Leu | Arg | Gly | Leu | |
| | | 115 | | | | | 120 | | | | | 125 | | | | |

| CCA | AGT | GAA | ACC | ATA | ATT | AAG | GCT | TTC | GAT | ATT | TTC | ACT | CGT | TCA | ATA | 432 |
| Pro | Ser | Glu | Thr | Ile | Ile | Lys | Ala | Phe | Asp | Ile | Phe | Thr | Arg | Ser | Ile | |
| | | 130 | | | | 135 | | | | | 140 | | | | | |

| ATA | ATT | ATA | TCC | GAA | GGA | CAG | GCA | GTA | GAT | ATG | GAA | TTT | GAG | GAC | AGA | 480 |
| Ile | Ile | Ile | Ser | Glu | Gly | Gln | Ala | Val | Asp | Met | Glu | Phe | Glu | Asp | Arg | |
| 145 | | | | | 150 | | | | | 155 | | | | | 160 | |

| ATT | GAT | ATA | AAG | GAG | CAG | GAA | TAC | CTT | GAC | ATG | ATC | TCA | CGT | AAG | ACA | 528 |
| Ile | Asp | Ile | Lys | Glu | Gln | Glu | Tyr | Leu | Asp | Met | Ile | Ser | Arg | Lys | Thr | |
| | | | | 165 | | | | | 170 | | | | | 175 | | |

| GCT | GCA | TTA | TTC | TCG | GCA | TCC | TCA | AGT | ATA | GGC | GCA | CTT | ATT | GCT | GGT | 576 |
| Ala | Ala | Leu | Phe | Ser | Ala | Ser | Ser | Ser | Ile | Gly | Ala | Leu | Ile | Ala | Gly | |
| | | | 180 | | | | | 185 | | | | | 190 | | | |

| GCT | AAT | GAT | AAT | GAT | GTA | AGA | CTG | ATG | TCT | GAT | TTC | GGT | ACG | AAT | CTA | 624 |
| Ala | Asn | Asp | Asn | Asp | Val | Arg | Leu | Met | Ser | Asp | Phe | Gly | Thr | Asn | Leu | |
| | | 195 | | | | | 200 | | | | | 205 | | | | |

| GGT | ATT | GCA | TTT | CAG | ATT | GTT | GAC | GAT | ATC | TTA | GGT | CTA | ACA | GCA | GAC | 672 |
| Gly | Ile | Ala | Phe | Gln | Ile | Val | Asp | Asp | Ile | Leu | Gly | Leu | Thr | Ala | Asp | |
| | | 210 | | | | | 215 | | | | | 220 | | | | |

| GAA | AAG | GAA | CTT | GGA | AAG | CCT | GTT | TTT | AGT | GAT | ATT | AGG | GAG | GGT | AAA | 720 |
| Glu | Lys | Glu | Leu | Gly | Lys | Pro | Val | Phe | Ser | Asp | Ile | Arg | Glu | Gly | Lys | |
| 225 | | | | | 230 | | | | | 235 | | | | | 240 | |

| AAG | ACT | ATA | CTT | GTA | ATA | AAA | ACA | CTG | GAG | CTT | TGT | AAA | GAG | GAC | GAG | 768 |
| Lys | Thr | Ile | Leu | Val | Ile | Lys | Thr | Leu | Glu | Leu | Cys | Lys | Glu | Asp | Glu | |
| | | | | 245 | | | | | 250 | | | | | 255 | | |

| AAG | AAG | ATT | GTC | CTA | AAG | GCG | TTA | GGT | AAT | AAG | TCA | GCC | TCA | AAA | GAA | 816 |
| Lys | Lys | Ile | Val | Leu | Lys | Ala | Leu | Gly | Asn | Lys | Ser | Ala | Ser | Lys | Glu | |
| | | | | 260 | | | | | 265 | | | | | 270 | | |

| GAA | TTA | ATG | AGC | TCA | GCA | GAT | ATA | ATT | AAG | AAA | TAC | TCT | TTA | GAT | TAT | 864 |
| Glu | Leu | Met | Ser | Ser | Ala | Asp | Ile | Ile | Lys | Lys | Tyr | Ser | Leu | Asp | Tyr | |

|     |     |     |     | 275 |     |     |     | 280 |     |     |     | 285 |     |     |     |     |
|-----|-----|-----|-----|-----|-----|-----|-----|-----|-----|-----|-----|-----|-----|-----|-----|-----|
| GCA | TAC | AAT | TTA | GCA | GAG | AAA | TAT | TAT | AAA | AAT | GCT | ATA | GAC | TCT | TTA | 912 |
| Ala | Tyr | Asn | Leu | Ala | Glu | Lys | Tyr | Tyr | Lys | Asn | Ala | Ile | Asp | Ser | Leu |     |
| 290 |     |     |     |     | 295 |     |     |     |     | 300 |     |     |     |     |     |     |

| AAT | CAA | GTC | TCC | TCT | AAG | AGT | GAT | ATA | CCT | GGA | AAG | GCT | TTA | AAA | TAT | 960 |
|-----|-----|-----|-----|-----|-----|-----|-----|-----|-----|-----|-----|-----|-----|-----|-----|-----|
| Asn | Gln | Val | Ser | Ser | Lys | Ser | Asp | Ile | Pro | Gly | Lys | Ala | Leu | Lys | Tyr |     |
| 305 |     |     |     |     | 310 |     |     |     |     | 315 |     |     |     |     | 320 |     |

| CTA | GCT | GAA | TTT | ACG | ATA | AGA | AGG | AGA | AAA | TAA | 993 |
|-----|-----|-----|-----|-----|-----|-----|-----|-----|-----|-----|-----|
| Leu | Ala | Glu | Phe | Thr | Ile | Arg | Arg | Arg | Lys |     |     |
|     |     |     |     | 325 |     |     |     |     | 330 |     |     |

( 2 ) INFORMATION FOR SEQ ID NO:4:

( i ) SEQUENCE CHARACTERISTICS:
    ( A ) LENGTH:993
    ( B ) TYPE:Nucleic acid
    ( C ) STRANDEDNESS:Double strand
    ( D ) TOPOLOGY:Linear ( i i ) MOLECULE TYPE:Mutated genomic DNA ( x i ) SEQUENCE DESCRIPTION:SEQ ID NO:4:

| ATG | AGT | TAC | TTT | GAC | AAC | TAT | TTT | AAT | GAG | ATT | GTT | AAT | TCT | GTA | AAC | 48 |
|-----|-----|-----|-----|-----|-----|-----|-----|-----|-----|-----|-----|-----|-----|-----|-----|-----|
| Met | Ser | Tyr | Phe | Asp | Asn | Tyr | Phe | Asn | Glu | Ile | Val | Asn | Ser | Val | Asn |     |
|     |     |     |     | 5   |     |     |     |     | 10  |     |     |     |     | 15  |     |     |

| GAC | ATT | ATT | AAG | AGC | TAT | ATA | TCT | GGA | GAT | GTT | CCT | AAA | CTA | TAT | GAA | 96 |
|-----|-----|-----|-----|-----|-----|-----|-----|-----|-----|-----|-----|-----|-----|-----|-----|-----|
| Asp | Ile | Ile | Lys | Ser | Tyr | Ile | Ser | Gly | Asp | Val | Pro | Lys | Leu | Tyr | Glu |     |
|     |     |     | 20  |     |     |     |     | 25  |     |     |     |     | 30  |     |     |     |

| GCC | TCA | TAT | CAT | TTG | TTT | ACA | TCT | GGA | GGT | AAG | AGG | TTA | AGA | CCA | TTA | 144 |
|-----|-----|-----|-----|-----|-----|-----|-----|-----|-----|-----|-----|-----|-----|-----|-----|-----|
| Ala | Ser | Tyr | His | Leu | Phe | Thr | Ser | Gly | Gly | Lys | Arg | Leu | Arg | Pro | Leu |     |
|     |     |     | 35  |     |     |     |     | 40  |     |     |     |     | 45  |     |     |     |

| ATC | TTA | ACT | ATA | TCA | TCA | GAT | TTA | TTC | GGA | GGA | CAG | AGA | GAA | AGA | GCT | 192 |
|-----|-----|-----|-----|-----|-----|-----|-----|-----|-----|-----|-----|-----|-----|-----|-----|-----|
| Ile | Leu | Thr | Ile | Ser | Ser | Asp | Leu | Phe | Gly | Gly | Gln | Arg | Glu | Arg | Ala |     |
|     |     | 50  |     |     |     |     | 55  |     |     |     |     | 60  |     |     |     |     |

| TAT | TAT | GCA | GGT | GCA | GCT | ATT | GAA | GTT | CTT | CAT | ACT | TCT | ACG | CTT | GTG | 240 |
|-----|-----|-----|-----|-----|-----|-----|-----|-----|-----|-----|-----|-----|-----|-----|-----|-----|
| Tyr | Tyr | Ala | Gly | Ala | Ala | Ile | Glu | Val | Leu | His | Thr | Ser | Thr | Leu | Val |     |
| 65  |     |     |     |     | 70  |     |     |     |     | 75  |     |     |     |     | 80  |     |

| CAT | GAT | GAT | ATT | ATG | GAT | CAA | GAT | AAT | ATC | AGA | AGA | GGG | TTA | CCC | ACA | 288 |
|-----|-----|-----|-----|-----|-----|-----|-----|-----|-----|-----|-----|-----|-----|-----|-----|-----|
| His | Asp | Asp | Ile | Met | Asp | Gln | Asp | Asn | Ile | Arg | Arg | Gly | Leu | Pro | Thr |     |
|     |     |     |     | 85  |     |     |     |     | 90  |     |     |     |     | 95  |     |     |

| GTC | CAC | GTG | AAA | TAC | GGC | TTA | CCC | TTA | GCA | ATA | TTA | GCT | GGG | GAT | TTA | 336 |
|-----|-----|-----|-----|-----|-----|-----|-----|-----|-----|-----|-----|-----|-----|-----|-----|-----|
| Val | His | Val | Lys | Tyr | Gly | Leu | Pro | Leu | Ala | Ile | Leu | Ala | Gly | Asp | Leu |     |
|     |     |     | 100 |     |     |     |     | 105 |     |     |     |     | 110 |     |     |     |

| CTA | CAT | GCA | AAG | GCT | TTT | CAG | CTC | TTA | ACC | CAG | GCT | CTT | AGA | GGT | TTG | 384 |
|-----|-----|-----|-----|-----|-----|-----|-----|-----|-----|-----|-----|-----|-----|-----|-----|-----|
| Leu | His | Ala | Lys | Ala | Phe | Gln | Leu | Leu | Thr | Gln | Ala | Leu | Arg | Gly | Leu |     |
|     |     |     | 115 |     |     |     |     | 120 |     |     |     |     | 125 |     |     |     |

| CCA | AGT | GAA | ACC | ATA | ATT | AAG | GCT | TTC | GAT | ATT | TTC | ACT | CGT | TCA | ATA | 432 |
|-----|-----|-----|-----|-----|-----|-----|-----|-----|-----|-----|-----|-----|-----|-----|-----|-----|
| Pro | Ser | Glu | Thr | Ile | Ile | Lys | Ala | Phe | Asp | Ile | Phe | Thr | Arg | Ser | Ile |     |
|     |     | 130 |     |     |     |     | 135 |     |     |     |     | 140 |     |     |     |     |

| ATA | ATT | ATA | TCC | GAA | GGA | CAG | GCA | GTA | GAT | ATG | GAA | TTT | GAG | GAC | AGA | 480 |
|-----|-----|-----|-----|-----|-----|-----|-----|-----|-----|-----|-----|-----|-----|-----|-----|-----|
| Ile | Ile | Ile | Ser | Glu | Gly | Gln | Ala | Val | Asp | Met | Glu | Phe | Glu | Asp | Arg |     |
| 145 |     |     |     |     | 150 |     |     |     |     | 155 |     |     |     |     | 160 |     |

| ATT | GAT | ATA | AAG | GAG | CAG | GAA | TAC | CTT | GAC | ATG | ATC | TCA | CGT | AAG | ACA | 528 |
|-----|-----|-----|-----|-----|-----|-----|-----|-----|-----|-----|-----|-----|-----|-----|-----|-----|
| Ile | Asp | Ile | Lys | Glu | Gln | Glu | Tyr | Leu | Asp | Met | Ile | Ser | Arg | Lys | Thr |     |
|     |     |     |     | 165 |     |     |     |     | 170 |     |     |     |     | 175 |     |     |

| GCT | GCA | TTA | TTC | TCG | GCA | TCC | TCA | AGT | ATA | GGC | GCA | CTT | ATT | GCT | GGT | 576 |
|-----|-----|-----|-----|-----|-----|-----|-----|-----|-----|-----|-----|-----|-----|-----|-----|-----|
| Ala | Ala | Leu | Phe | Ser | Ala | Ser | Ser | Ser | Ile | Gly | Ala | Leu | Ile | Ala | Gly |     |
|     |     |     |     | 180 |     |     |     |     | 185 |     |     |     |     | 190 |     |     |

| GCT | AAT | GAT | AAT | GAT | GTA | AGA | CTG | ATG | TCT | GAT | TTC | GGT | ACG | AAT | CTA | 624 |
|-----|-----|-----|-----|-----|-----|-----|-----|-----|-----|-----|-----|-----|-----|-----|-----|-----|
| Ala | Asn | Asp | Asn | Asp | Val | Arg | Leu | Met | Ser | Asp | Phe | Gly | Thr | Asn | Leu |     |
|     |     |     | 195 |     |     |     |     | 200 |     |     |     |     | 205 |     |     |     |

| GGT | ATT | GCA | TTT | CAG | ATT | GTT | GAC | GAT | ATC | TTA | GGT | CTA | ACA | GCA | GAC | 672 |

```
Gly Ile Ala Phe Gln Ile Val Asp Asp Ile Leu Gly Leu Thr Ala Asp
    210                 215                 220

GAA AAG GAA CTT GGA AAG CCT GTT TTT AGT GAT ATT AGG GAG GGT AAA      720
Glu Lys Glu Leu Gly Lys Pro Val Phe Ser Asp Ile Arg Glu Gly Lys
225                 230                 235                 240

AAG ACT ATA CTT GTA ATA AAA ACA CTG GAG CTT TGT AAA GAG GAC GAG      768
Lys Thr Ile Leu Val Ile Lys Thr Leu Glu Leu Cys Lys Glu Asp Glu
                245                 250                 255

AAG AAG ATT GTC CTA AAG GCG TTA GGT AAT AAG TCA GCC TCA AAA GAA      816
Lys Lys Ile Val Leu Lys Ala Leu Gly Asn Lys Ser Ala Ser Lys Glu
            260                 265                 270

GAA TTA ATG AGC TCA GCA GAT ATA ATT AAG AAA TAC TCT TTA GAT TAT      864
Glu Leu Met Ser Ser Ala Asp Ile Ile Lys Lys Tyr Ser Leu Asp Tyr
        275                 280                 285

GCA TAC AAT TTA GCA GAG AAA TAT TAT AAA AAT GCT ATA GAC TCT TTA      912
Ala Tyr Asn Leu Ala Glu Lys Tyr Tyr Lys Asn Ala Ile Asp Ser Leu
    290                 295                 300

AAT CAA GTC TCC TCT AAG AGT GAT ATA CCT GGA AAG GCT TTA AAA TAT      960
Asn Gln Val Ser Ser Lys Ser Asp Ile Pro Gly Lys Ala Leu Lys Tyr
305                 310                 315                 320

CTA GCT GAA TTT ACG ATA AGA AGG AGA AAA TAA                          993
Leu Ala Glu Phe Thr Ile Arg Arg Arg Lys
                325                 330
```

(2) INFORMATION FOR SEQ ID NO:5:

(i) SEQUENCE CHARACTERISTICS:
        (A) LENGTH:993
        (B) TYPE:Nucleic acid
        (C) STRANDEDNESS:Double strand
        (D) TOPOLOGY:Linear (ii) MOLECULE TYPE:Mutated genomic DNA (xi) SEQUENCE DESCRIPTION: SEQ ID NO:5:

```
ATG AGT TAC TTT GAC AAC TAT TTT AAT GAG ATT GTT AAT TCT GTA AAC       48
Met Ser Tyr Phe Asp Asn Tyr Phe Asn Glu Ile Val Asn Ser Val Asn
                5                  10                  15

GAC ATT ATT AAG AGC TAT ATA TCT GGA GAT GTT CCT AAA CTA TAT GAA       96
Asp Ile Ile Lys Ser Tyr Ile Ser Gly Asp Val Pro Lys Leu Tyr Glu
            20                  25                  30

GCC TCA TAT CAT TTG TTT ACA TCT GGA GGT AAG AGG TTA AGA CCA TTA      144
Ala Ser Tyr His Leu Phe Thr Ser Gly Gly Lys Arg Leu Arg Pro Leu
        35                  40                  45

ATC TTA ACT ATA TCA TCA GAT TTA TTC GGA GGA CAG AGA GAA AGA GCT      192
Ile Leu Thr Ile Ser Ser Asp Leu Phe Gly Gly Gln Arg Glu Arg Ala
    50                  55                  60

TAT TAT GCA GGT GCA GCT ATT GAA GTT CTT CAT ACT CTT ACG CTT GTG      240
Tyr Tyr Ala Gly Ala Ala Ile Glu Val Leu His Thr Leu Thr Leu Val
65                  70                  75                  80

CAT GAT GAT ATT ATG GAT CAA GAT AAT ATC AGA AGA GGG TTA CCC ACA      288
His Asp Asp Ile Met Asp Gln Asp Asn Ile Arg Arg Gly Leu Pro Thr
                85                  90                  95

GTC CAC ATG AAA TAC GGC TTA CCC TTA GCA ATA TTA GCT GGG GAT TTA      336
Val His Met Lys Tyr Gly Leu Pro Leu Ala Ile Leu Ala Gly Asp Leu
            100                 105                 110

CTA CAT GCA AAG GCT TTT CAG CTC TTA ACC CAG GCT CTT AGA GGT TTG      384
Leu His Ala Lys Ala Phe Gln Leu Leu Thr Gln Ala Leu Arg Gly Leu
        115                 120                 125

CCA AGT GAA ACC ATA ATT AAG GCT TTC GAT ATT TTC ACT CGT TCA ATA      432
Pro Ser Glu Thr Ile Ile Lys Ala Phe Asp Ile Phe Thr Arg Ser Ile
    130                 135                 140
```

| | | | | | | | | | | | | | | | | |
|---|---|---|---|---|---|---|---|---|---|---|---|---|---|---|---|---|
| ATA | ATT | ATA | TCC | GAA | GGA | CAG | GCA | GTA | GAT | ATG | GAA | TTT | GAG | GAC | AGA | 480 |
| Ile | Ile | Ile | Ser | Glu | Gly | Gln | Ala | Val | Asp | Met | Glu | Phe | Glu | Asp | Arg | |
| 145 | | | | 150 | | | | | 155 | | | | | | 160 | |
| ATT | GAT | ATA | AAG | GAG | CAG | GAA | TAC | CTT | GAC | ATG | ATC | TCA | CGT | AAG | ACA | 528 |
| Ile | Asp | Ile | Lys | Glu | Gln | Glu | Tyr | Leu | Asp | Met | Ile | Ser | Arg | Lys | Thr | |
| | | | 165 | | | | | 170 | | | | | 175 | | | |
| GCT | GCA | TTA | TTC | TCG | GCA | TCC | TCA | AGT | ATA | GGC | GCA | CTT | ATT | GCT | GGT | 576 |
| Ala | Ala | Leu | Phe | Ser | Ala | Ser | Ser | Ser | Ile | Gly | Ala | Leu | Ile | Ala | Gly | |
| | | | 180 | | | | | 185 | | | | | 190 | | | |
| GCT | AAT | GAT | AAT | GAT | GTA | AGA | CTG | ATG | TCT | GAT | TTC | GGT | ACG | AAT | CTA | 624 |
| Ala | Asn | Asp | Asn | Asp | Val | Arg | Leu | Met | Ser | Asp | Phe | Gly | Thr | Asn | Leu | |
| | | 195 | | | | | 200 | | | | | 205 | | | | |
| GGT | ATT | GCA | TTT | CAG | ATT | GTT | GAC | GAT | ATC | TTA | GGT | CTA | ACA | GCA | GAC | 672 |
| Gly | Ile | Ala | Phe | Gln | Ile | Val | Asp | Asp | Ile | Leu | Gly | Leu | Thr | Ala | Asp | |
| | 210 | | | | 215 | | | | | 220 | | | | | | |
| GAA | AAG | GAA | CTT | GGA | AAG | CCT | GTT | TTT | AGT | GAT | ATT | AGG | GAG | GGT | AAA | 720 |
| Glu | Lys | Glu | Leu | Gly | Lys | Pro | Val | Phe | Ser | Asp | Ile | Arg | Glu | Gly | Lys | |
| 225 | | | | 230 | | | | | 235 | | | | | | 240 | |
| AAG | ACT | ATA | CTT | GTA | ATA | AAA | ACA | CTG | GAG | CTT | TGT | AAA | GAG | GAC | GAG | 768 |
| Lys | Thr | Ile | Leu | Val | Ile | Lys | Thr | Leu | Glu | Leu | Cys | Lys | Glu | Asp | Glu | |
| | | | 245 | | | | | 250 | | | | | 255 | | | |
| AAG | AAG | ATT | GTC | CTA | AAG | GCG | TTA | GGT | AAT | AAG | TCA | GCC | TCA | AAA | GAA | 816 |
| Lys | Lys | Ile | Val | Leu | Lys | Ala | Leu | Gly | Asn | Lys | Ser | Ala | Ser | Lys | Glu | |
| | | | 260 | | | | 265 | | | | | 270 | | | | |
| GAA | TTA | ATG | AGC | TCA | GCA | GAT | ATA | ATT | AAG | AAA | TAC | TCT | TTA | GAT | TAT | 864 |
| Glu | Leu | Met | Ser | Ser | Ala | Asp | Ile | Ile | Lys | Lys | Tyr | Ser | Leu | Asp | Tyr | |
| | | 275 | | | | | 280 | | | | | 285 | | | | |
| GCA | TAC | AAT | TTA | GCA | GAG | AAA | TAT | TAT | AAA | AAT | GCT | ATA | GAC | TCT | TTA | 912 |
| Ala | Tyr | Asn | Leu | Ala | Glu | Lys | Tyr | Tyr | Lys | Asn | Ala | Ile | Asp | Ser | Leu | |
| | 290 | | | | | 295 | | | | | 300 | | | | | |
| AAT | CAA | GTC | TCC | TCT | AAG | AGT | GAT | ATA | CCT | GGA | AAG | GCT | TTA | AAA | TAT | 960 |
| Asn | Gln | Val | Ser | Ser | Lys | Ser | Asp | Ile | Pro | Gly | Lys | Ala | Leu | Lys | Tyr | |
| 305 | | | | 310 | | | | | 315 | | | | | | 320 | |
| CTA | GCT | GAA | TTT | ACG | ATA | AGA | AGG | AGA | AAA | TAA | | | | | | 993 |
| Leu | Ala | Glu | Phe | Thr | Ile | Arg | Arg | Arg | Lys | | | | | | | |
| | | | | 325 | | | | | 330 | | | | | | | |

( 2 ) INFORMATION FOR SEQ ID NO:6:

( i ) SEQUENCE CHARACTERISTICS:
        ( A ) LENGTH:993
        ( B ) TYPE:Nucleic acid
        ( C ) STRANDEDNESS:Double strand
        ( D ) TOPOLOGY:Linear ( i i ) MOLECULE TYPE:Mutated genomic DNA ( x i ) SEQUENCE DESCRIPTION:SEQ ID NO:6:

| | | | | | | | | | | | | | | | | |
|---|---|---|---|---|---|---|---|---|---|---|---|---|---|---|---|---|
| ATG | AGT | TAC | TTT | GAC | AAC | TAT | TTT | AAT | GAG | ATT | GTT | AAT | TCT | GTA | AAC | 48 |
| Met | Ser | Tyr | Phe | Asp | Asn | Tyr | Phe | Asn | Glu | Ile | Val | Asn | Ser | Val | Asn | |
| | | | | 5 | | | | | 10 | | | | | 15 | | |
| GAC | ATT | ATT | AAG | AGC | TAT | ATA | TCT | GGA | GAT | GTT | CCT | AAA | CTA | TAT | GAA | 96 |
| Asp | Ile | Ile | Lys | Ser | Tyr | Ile | Ser | Gly | Asp | Val | Pro | Lys | Leu | Tyr | Glu | |
| | | | 20 | | | | | 25 | | | | | 30 | | | |
| GCC | TCA | TAT | CAT | TTG | TTT | ACA | TCT | GGA | GGT | AAG | AGG | TTA | AGA | CCA | TTA | 144 |
| Ala | Ser | Tyr | His | Leu | Phe | Thr | Ser | Gly | Gly | Lys | Arg | Leu | Arg | Pro | Leu | |
| | | 35 | | | | | 40 | | | | | 45 | | | | |
| ATC | TTA | ACT | ATA | TCA | TCA | GAT | TTA | TTC | GGA | GGA | CAG | AGA | GAA | AGA | GCT | 192 |
| Ile | Leu | Thr | Ile | Ser | Ser | Asp | Leu | Phe | Gly | Gly | Gln | Arg | Glu | Arg | Ala | |
| | | 50 | | | | | 55 | | | | | 60 | | | | |
| TAT | TAT | GCA | GGT | GCA | GCT | ATT | GAA | GTT | CTT | CAT | ACT | TCT | ACG | CTT | GTG | 240 |
| Tyr | Tyr | Ala | Gly | Ala | Ala | Ile | Glu | Val | Leu | His | Thr | Ser | Thr | Leu | Val | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| CAT | GAT | GAT | ATT | ATG | GAT | CAA | GAT | AAT | ATC | AGA | AGA | GGG | TTA | CCC | ACA | 288 |
| His | Asp | Asp | Ile | Met | Asp | Gln | Asp | Asn | Ile | Arg | Arg | Gly | Leu | Pro | Thr | |
| | | | | 85 | | | | | 90 | | | | | 95 | | |
| GTC | CAC | GTG | AAA | CAC | GGC | TTA | CCC | TTA | GCA | ATA | TTA | GCT | GGG | GAT | TTA | 336 |
| Val | His | Val | Lys | His | Gly | Leu | Pro | Leu | Ala | Ile | Leu | Ala | Gly | Asp | Leu | |
| | | | 100 | | | | | 105 | | | | | 110 | | | |
| CTA | CAT | GCA | AAG | GCT | TTT | CAG | CTC | TTA | ACC | CAG | GCT | CTT | AGA | GGT | TTG | 384 |
| Leu | His | Ala | Lys | Ala | Phe | Gln | Leu | Leu | Thr | Gln | Ala | Leu | Arg | Gly | Leu | |
| | | 115 | | | | | 120 | | | | | 125 | | | | |
| CCA | AGT | GAA | ACC | ATA | ATT | AAG | GCT | TTC | GAT | ATT | TTC | ACT | CGT | TCA | ATA | 432 |
| Pro | Ser | Glu | Thr | Ile | Ile | Lys | Ala | Phe | Asp | Ile | Phe | Thr | Arg | Ser | Ile | |
| | 130 | | | | | 135 | | | | | 140 | | | | | |
| ATA | ATT | ATA | TCC | GAA | GGA | CAG | GCA | GTA | GAT | ATG | GAA | TTT | GAG | GAC | AGA | 480 |
| Ile | Ile | Ile | Ser | Glu | Gly | Gln | Ala | Val | Asp | Met | Glu | Phe | Glu | Asp | Arg | |
| 145 | | | | | 150 | | | | | 155 | | | | | 160 | |
| ATT | GAT | ATA | AAG | GAG | CAG | GAA | TAC | CTT | GAC | ATG | ATC | TCA | CGT | AAG | ACA | 528 |
| Ile | Asp | Ile | Lys | Glu | Gln | Glu | Tyr | Leu | Asp | Met | Ile | Ser | Arg | Lys | Thr | |
| | | | | 165 | | | | | 170 | | | | | 175 | | |
| GCT | GCA | TTA | TTC | TCG | GCA | TCC | TCA | AGT | ATA | GGC | GCA | CTT | ATT | GCT | GGT | 576 |
| Ala | Ala | Leu | Phe | Ser | Ala | Ser | Ser | Ser | Ile | Gly | Ala | Leu | Ile | Ala | Gly | |
| | | | 180 | | | | | 185 | | | | | 190 | | | |
| GCT | AAT | GAT | AAT | GAT | GTA | AGA | CTG | ATG | TCT | GAT | TTC | GGT | ACG | AAT | CTA | 624 |
| Ala | Asn | Asp | Asn | Asp | Val | Arg | Leu | Met | Ser | Asp | Phe | Gly | Thr | Asn | Leu | |
| | | 195 | | | | | 200 | | | | | 205 | | | | |
| GGT | ATT | GCA | TTT | CAG | ATT | GTT | GAC | GAT | ATC | TTA | GGT | CTA | ACA | GCA | GAC | 672 |
| Gly | Ile | Ala | Phe | Gln | Ile | Val | Asp | Asp | Ile | Leu | Gly | Leu | Thr | Ala | Asp | |
| | 210 | | | | | 215 | | | | | 220 | | | | | |
| GAA | AAG | GAA | CTT | GGA | AAG | CCT | GTT | TTT | AGT | GAT | ATT | AGG | GAG | GGT | AAA | 720 |
| Glu | Lys | Glu | Leu | Gly | Lys | Pro | Val | Phe | Ser | Asp | Ile | Arg | Glu | Gly | Lys | |
| 225 | | | | | 230 | | | | | 235 | | | | | 240 | |
| AAG | ACT | ATA | CTT | GTA | ATA | AAA | ACA | CTG | GAG | CTT | TGT | AAA | GAG | GAC | GAG | 768 |
| Lys | Thr | Ile | Leu | Val | Ile | Lys | Thr | Leu | Glu | Leu | Cys | Lys | Glu | Asp | Glu | |
| | | | | 245 | | | | | 250 | | | | | 255 | | |
| AAG | AAG | ATT | GTC | CTA | AAG | GCG | TTA | GGT | AAT | AAG | TCA | GCC | TCA | AAA | GAA | 816 |
| Lys | Lys | Ile | Val | Leu | Lys | Ala | Leu | Gly | Asn | Lys | Ser | Ala | Ser | Lys | Glu | |
| | | | 260 | | | | | 265 | | | | | 270 | | | |
| GAA | TTA | ATG | AGC | TCA | GCA | GAT | ATA | ATT | AAG | AAA | TAC | TCT | TTA | GAT | TAT | 864 |
| Glu | Leu | Met | Ser | Ser | Ala | Asp | Ile | Ile | Lys | Lys | Tyr | Ser | Leu | Asp | Tyr | |
| | | 275 | | | | | 280 | | | | | 285 | | | | |
| GCA | TAC | AAT | TTA | GCA | GAG | AAA | TAT | TAT | AAA | AAT | GCT | ATA | GAC | TCT | TTA | 912 |
| Ala | Tyr | Asn | Leu | Ala | Glu | Lys | Tyr | Tyr | Lys | Asn | Ala | Ile | Asp | Ser | Leu | |
| | 290 | | | | | 295 | | | | | 300 | | | | | |
| AAT | CAA | GTC | TCC | TCT | AAG | AGT | GAT | ATA | CCT | GGA | AAG | GCT | TTA | AAA | TAT | 960 |
| Asn | Gln | Val | Ser | Ser | Lys | Ser | Asp | Ile | Pro | Gly | Lys | Ala | Leu | Lys | Tyr | |
| 305 | | | | | 310 | | | | | 315 | | | | | 320 | |
| CTA | GCT | GAA | TTT | ACG | ATA | AGA | AGG | AGA | AAA | TAA | | | | | | 993 |
| Leu | Ala | Glu | Phe | Thr | Ile | Arg | Arg | Arg | Lys | | | | | | | |
| | | | | 325 | | | | | 330 | | | | | | | |

( 2 ) INFORMATION FOR SEQ ID NO:7:

( i ) SEQUENCE CHARACTERISTICS:
        ( A ) LENGTH:26
        ( B ) TYPE: Nucleic acid
        ( C ) STRANDEDNESS:Single strand
        ( D ) TOPOLOGY:Linear ( i i ) MOLECULE TYPE:Synthetic DNA ( x i ) SEQUENCE DESCRIPTION:SEQ ID NO:7:

AAGAGAAGCT TATGAGTTAC TTTGAC                      26

( 2 ) INFORMATION FOR SEQ ID NO:8:

( i ) SEQUENCE CHARACTERISTICS:
        ( A ) LENGTH:21
        ( B ) TYPE:Nucleic acid
        ( C ) STRANDEDNESS:Single strand
        ( D ) TOPOLOGY:Linear ( i i ) MOLECULE TYPE:Synthetic DNA ( x i ) SEQUENCE DESCRIPTION: SEQ ID NO:8:

GATACAAGCT TTATTTTCTC C                            2 1

( 2 ) INFORMATION FOR SEQ ID NO:9:

( i ) SEQUENCE CHARACTERISTICS:
        ( A ) LENGTH:28
        ( B ) TYPE:Nucleic acid
        ( C ) STRANDEDNESS:Single strand
        ( D ) TOPOLOGY:Linear ( i i ) MOLECULE TYPE:Synthetic DNA ( x i ) SEQUENCE DESCRIPTION:SEQ ID NO:9:

CCCCCCTCGA GGTCGACGGT ATCGATAA                    2 8

NUCLEIC ACID ENCODING MUTANT GERANYLGERANYL DIPHOSPHATE SYNTHASE

This application is a division of allowed application Ser. No. 08/705,377 filed Aug. 29, 1996, now U.S. Pat. No. 5,807,725, the entirety of which is incorporated herein by reference.

BACKGROUND OF INVENTION

1. Field of Invention

The present invention relates to a mutant prenyl diphosphate synthase that is able to synthesize prenyl diphosphate having a longer chain than prenyl diphosphate synthesized by the native prenyl diphosphate synthase.

2. Related Art

Prenyl diphosphate is highly valuable in biosynthesis pathways, functioning as a precursor of steroids, a precursor of carotenoids, being a transition substrate of prenylated proteins, being a substrate for synthesis of vitamin E, vitamin K and ubiquinone (CoQ) and so forth. Prenyl diphosphate exists in various forms, including dimethylallyl diphosphate (DMAPP; C5), geranyl diphosphate (GPP; C10), farnesyl diphosphate (FPP; C15), geranylgeranyl diphosphate (GGPP; C20), geranylfarnesyl diphosphate (GFPP; C25), hexaprenyl diphosphate (HPP; C30), heptaprenyl diphosphate (HepPP; C35) and octaprenyl diphosphate (OPP; C40).

Prenyl transferases, which synthesize these prenyl diphosphates, are enzymes that form prenyl diphosphate by continuously condensing isopentenyl diphosphate (IPP; C5) into allylic diphosphate, and exist in various forms, including farnesyl diphosphate synthase (FPS), geranylgeranyl diphosphate synthase (GGPS), geranylfarnesyl diphosphate synthase (GFPS), hexaprenyl diphosphate synthase (HexPS), heptaprenyl diphosphate synthase (HepPS) and octaprenyl diphosphate synthase (OPS).

However, among the above-mentioned prenyl diphosphates, only those from dimethylallyl diphosphate having 5 carbon atoms to geranyl diphosphate having 20 carbon atoms are commercially available in small amounts as reagents, and a process for industrially synthesizing and recovering large amounts of prenyl diphosphates having longer chains is not known.

The carbon chain length and stereoisomerism of synthesized prenyl diphosphates are known to be specifically determined depending on the particular enzyme. Until now, it has not been clear what type of mechanism is the factor in determining carbon chain length.

Although prenyl transferases and their genes are known to be derived from bacteria, mold, plants and animals, these enzyme are typically unstable, difficult to handle and are not expected to be industrially valuable.

The prenyl transferases and their genes of thermophilic organisms, which are stable and easy to use as enzymes, are only farnesyl diphosphate synthase (FPS) (Koyama, T. et al. (1995) J. Biol. Chem. 113, 355–363) and heptaprenyl diphosphate synthase (HepPS) (Koike-Takeshita, A. et al. (1995) J. Biol. Chem. 270, 18396–18400) from the moderately thermophilic archaebacterium, *Bacillus stearothermophilus*; geranylgeranyl diphosphate synthase (GGPS) from the hyper thermophilic bacterium, *Sulfolobus acidocaldarius* (Ohnuma, S.-i. et al. (1994) J. Biol. Chem. 268, 14792–14797); as well as farnesyl diphosphate/geranylgeranyl diphosphate synthase (FPS/GGPS) from the methane-producing archaebacterium, *Methanobacterium thermoautotrophicum* (Chen, A. and Poulter, C. D. (1993) J. Biol. Chem. 268, 11002–11007). Only HepPS can synthesize prenyl diphosphate having 35 carbon atoms, and enzymes having thermal stability that synthesize prenyl diphosphates having 25 or more carbon atoms have not been reported. In addition, the above-mentioned HepPS does not have adequate heat resistance, is composed of two types of subunits, and handling is not always easy.

SUMMARY OF INVENTION

Thus, the present invention provides a thermostable prenyl diphosphate synthase capable of synthesizing long-chain prenyl diphosphate, a process for its production, and a method for using said enzyme.

In order to create an enzyme that can synthesize prenyl diphosphate having a longer chain length, the inventors of the present invention succeeded in creating a mutant enzyme able to synthesize prenyl diphosphate having a longer chain than naturally-occurring geranylgeranyl diphosphate synthase by treating DNA coding for geranylgeranyl diphosphate synthase with a mutation agent, introducing the above-mentioned treated DNA into the yeast, *Saccharomyces cerevisiae*, deficient for hexaprenyl diphosphate synthase activity, and selecting a mutant DNA that can complement the above-mentioned deficient, and moreover, elucidated the relationship between the mutation site in the enzyme and the chain length of the prenyl diphosphate that is formed, thereby leading to completion of the present invention.

Thus, the present invention provides a mutant enzyme wherein, least one of phenylalanine residue at position 77, methionine residue at position 85, valine residue at position 99, tyrosine residue at position 101, phenylalanine residue at position 118, Arginine residue at position 199 and aspartic acid residue at position 312 in a geranylgeranyl diphosphate synthase of *Sulfolobus acidocaldarius* origin is substituted with another amino acid, and which enzyme can synthesize prenyl diphosphate having at least 25 carbon atoms.

Moreover, the present invention provides a gene system that codes for the above-mentioned enzyme, and a process for producing the above-mentioned enzyme using that gene system.

Furthermore, the present invention provides a process for producing a mutant prenyl diphosphate synthase comprising the steps of culturing a host transformed with a gene in which the codon for phenylalanine residue located at the fifth N-terminal side position from the N-terminal amino acid of the aspartate-rich domain I in a gene that codes for the native enzyme, is converted to a codon for a non-aromatic amino acid, thereby enabling the expression of a mutant enzyme that is able to synthesize prenyl diphosphates having a longer chain than the longest chain of prenyl diphosphate synthesized by the native prenyl diphosphate synthase.

In addition, the present invention provides a process for producing long-chain prenyl diphosphate using the above-mentioned enzyme.

DETAILED DESCRIPTION

Figure 1:
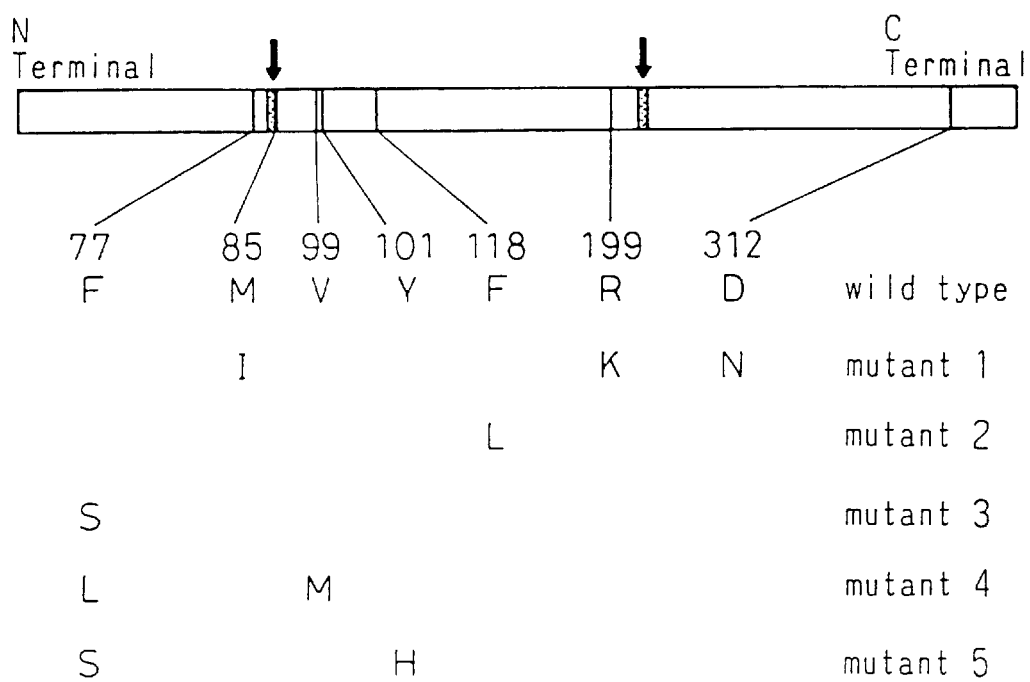
FIG. 1 indicates the mutation site of the present invention in the geranyl diphosphate synthase derived from *Sulfolobus acidocaldarius*. The arrows in the drawing indicate two aspartate-rich domains

As a specific example in the present invention, a geranylgeranyl diphosphate synthase (GGPS) gene of the hyper thermophilic archaebacterium, Sulfolobus acidocaldarius, is used for the starting material. The cloning method of this gene is described in detail in the specification of Japanese Patent Application No. 6-315572. In addition, another example for cloning the gene is described in the present specification as Example 1, and a nucleotide sequence and an amino acid sequence encoded thereby are shown as SEQ ID NO: 1.

In the present invention, a cloned DNA is mutated in vitro. Although chemical treatment using a mutagen, or physical treatment using UV light or X-rays can be used for the mutation means, chemical treatment is convenient to carry out. Any routinely used chemical mutagen can be used for the mutagenesis for the present invention, an example of which is nitrite.

A specific example of mutagenesis is shown in Example 2.

The mutagenized DNA is inserted into a yeast expression vector to prepare a DNA library. Any vector that is able to express an inserted extraneous gene in the yeast can be used as an expression vector, examples of which include a yeast plasmid such as pYEUra3 (available from Clonetech) and pYES2 (available from Invitrogen).

The resulting plasmid library is introduced into a yeast mutant strain defective for the ability to synthesize hexaprenyl diphosphate, which is one of the precursors of coenzyme Q6. Since this mutant strain is unable to synthesize coenzyme Q6 necessary for non-fermentative sugar metabolism, it cannot be grown in medium that contains glycerol as the sole carbon source. Thus, if the yeast transformed by the above-mentioned library is cultured in glycerol medium and the strains that grow are selected, strains can be selected that have acquired the ability to synthesize prenyl diphosphate having a large number of carbon atoms for coenzyme Q synthesis.

Five positive clones were obtained in this manner from approximately 1400 transformants. As a result of purifying the plasmids from these clones, determining the nucleotide sequence of the inserted fragment, and predicting amino acid sequences that are coded, each mutant had changes in the amino acid sequence as indicated below.

Mutant 1: Methionine at position 85 changed to isoleucine, arginine at position 199 changed to lysine, aspartic acid at position 312 changed to Asn Mutant 2: Phenylalanine at position 118 changed to leucine Mutant 3: Phenylalanine at position 77 changed to serine Mutant 4: Phenylanine at position 77 changed to leucine and valine at position 99 changed to methionine Mutant 5: Phenylalanine at position 77 changed to serine and tyrosine at position 101 changed to histidine In contrast to wild-type enzymes being unable to synthesize prenyl diphosphate having at least 25 carbon atoms, enzymes having amino acid sequences containing these changes were able to synthesize prenyl diphosphate having 25 or more carbon atoms. Those amino acid sequences having the above-mentioned amino acid substitutions are shown in SEQ ID NOs: 2 to 6.

Thus, it can be logically surmised that if an amino acid at any one of the above-mentioned positions is replaced with another amino acid, a prenyl diphosphate having more carbon atoms than that synthesized by the native enzyme can be synthesized. Thus, the present invention provides a mutant enzyme in which at least one amino acid from among phenylalanine at position 77, methionine at position 85, valine at position 99, tyrosine at position 101, phenylalanine at position 118, arginine at position 199 and aspartic acid at position 312 is replaced with another amino acid, and said enzyme is able to synthesize prenyl diphosphate having at least 25 carbon atoms Particularly in the case that phenylalanine at position 77 is replaced with another amino acid, and preferably a non-aromatic amino acid such as serine or leucine, that enzyme is able to synthesize prenyl diphosphate having at least 25 carbon atoms. Thus, in one embodiment, the present invention provides an enzyme in which at least phenylalanine at position 77 is replaced with another amino acid such as serine, leucine or another non-aromatic amino acid. This type of enzyme includes enzymes in which replaced amino acids are present at one or a plurality of the other above-mentioned positions. Examples of other amino acid positions include valine at position 99 and/or tyrosine at position 101.

Thus, the present invention includes enzymes in which only phenylalanine at position 77 is replaced, enzymes in which phenylalanine at position 77 and valine at position 99 are replaced, enzymes in which phenylalanine at position 77 and tyrosine at position 101 are replaced, enzymes in which phenylalanine at position 77, valine at position 99 and tyrosine at position 101 are replaced, and enzymes in which phenylalanine at position 77 and one or a plurality of amino acids at the above-mentioned positions are replaced.

According to another mode of the present invention, an enzyme in which methionine at position 85, arginine at position 199 and aspartic acid at position 312 are replaced with other amino acids is also able to synthesize prenyl diphosphate having at least 25 carbon atoms. Thus, the present invention, in another embodiment, includes an enzyme in which at least methionine at position 85, arginine at position 199 and aspartic acid at position 312 are replaced with other amino acids. In this embodiment, enzymes in which methionine at position 85, arginine at position 199 and aspartic acid at position 312 are replaced, as well as enzymes containing amino acid replacements at one or a plurality of sites other than at these sites or the above-mentioned mutation sites, are included.

According to still another embodiment of the present invention, an enzyme in which phenylalanine at position 118 is replaced with another amino acid can also synthesize prenyl diphosphate having at least 25 carbon atoms. Thus, in another embodiment, the present invention includes enzymes in which at least the amino acid at position 118 is replaced with another amino acid. In this embodiment, enzymes in which the amino acid at position 118 is replaced with another amino acid, as well as enzymes containing amino acid replacements at one or a plurality of positions of the above-mentioned amino acid replacement positions, are included.

Enzymes are known to have those own specificities of enzyme activities even in the case of being modified by addition, removal and/or replacement of one or a few amino acids. Thus, in addition to the peptides having the amino acid sequences shown in SEQ ID NOs; 2 to 6, the present invention also includes enzymes that the same specificity while having an amino acid sequence that is changed by replacing, deleting and/or adding one or a few, such as up to 5 or up to 10, amino acids with respect to the amino acid sequences shown in SEQ ID Nos: 2 to 6.

Two aspartate-rich domains (sites indicated with arrows in FIG. 1) are conserved in various prenyl transferases, and the diphosphate site of the substrate is thought to bind to these sites. Phenylalanine at position 77 exists at the 5th position upstream to the N-terminal side from the N-terminal of aspartate-rich domain I present on the N-terminal side among these two aspartate-rich domains. This phenylalanine is replaced with a non-aromatic amino acid in 3 of the 5 mutants of the present invention.

Thus, in order to synthesize prenyl diphosphate having a large number of carbon atoms, for example that having 25 or more carbon atoms, if phenylalanine at about the fifth position upstream to the N-terminal side from the amino acid of the N-terminal of aspartate-rich domain I is replaced with another amino acid, for example a non-aromatic amino acid, even in the case of a prenyl transferase other than the prenyl transferase derived from *Sulfolobus acidocaldarius* having the amino acid sequence indicated in Sequence No. 1, an enzyme is obtained that is able to synthesize prenyl diphosphate having a larger number of carbon atoms than the wild type enzyme.

Thus, the present invention provides a process for producing a mutant prenyl transferase characterized by replacing phenylalanine at the 5th position upstream to the N-terminal side from the amino acid of the N-terminal of aspartate-rich domain I of prenyl transferase. This amino acid replacement can be performed by changing the codon that codes for that amino acid.

In addition, the present invention provides a gene coding for the various above-mentioned mutant enzymes, a vector comprising that gene, particularly an expression vector, and a host transformed with said vector. The gene (DNA) of the present invention can be easily obtained by introducing a mutation into DNA that codes for the wild type amino acid sequence indicated in SEQ ID NO: 1, according to routine methods such as site-directed mutagenesis or PCR.

Moreover, once the amino acid sequence of the target enzyme has been determined, a suitable nucleotide sequence that codes for it can be determined, thus making the mutant is possible to chemically synthesize DNA by conventional DNA synthesis methods.

In addition, the present invention provides an expression vector comprising the DNA as described above, hosts transformed with said expression vector, and a process for producing an enzyme or peptide of the present invention using these hosts.

Although expression vectors contain an origin of replication, expression control sequence and so forth, these vary according to the host. Examples of hosts include procaryotes, examples of which include bacteria such as *E. coli* and Bacillus sp. including *Bacillus subtilus*; eucaryotes, examples of which include yeasts such as Saccharomyces sp. including *S. cerevisiae*, and Pichia sp. including *Pichia pastoris*; molds, examples of which include Asoeraillus sp. such as *A. oryzae* and *A. niger*; animal cells, examples of which include cultured cells and cultured cells of higher animals, such as CHO cells. In addition, it is also possible to use plants for the host.

According to the present invention, as indicated in Examples, geranylfarnesyl diphosphate can be accumulated in the culture by culturing a host transformed by the DNA of the present invention, and geranylfarnesyl diphosphate can be produced by recovering it from the culture. Also according to the present invention, geranylfarnesyl diphosphate can be produced by allowing the mutant GGPP synthase produced according to the process of the present invention to act on the isopentenyl diphosphate substrate and each allylic substrate such as farnesyl diphosphate.

In an example of using *E. coli* for the host, gene regulation of gene expression is known to exist such as in the process of transcribing mRNA from DNA and the process of translating protein from mRNA. In addition to those sequences present in nature (e.g. lac, trp, bla, lpp, $P_L$, $P_R$, ter, T3 and T7 as promoters), sequences in which their mutants (e.g. lacUV5) are artificially joined with wild type promoter sequences (e.g. tac, trc) are known as examples of promoter sequences that regulate mRNA transcription, and these can also be used in the present invention.

It is known that the ribosome binding site (GAGG and other similar sequences) sequence and the distance to the initiation codon are important as sequences that regulate the activity to translate the mRNA to synthesize proteins. In addition, it is also well known that the terminator, which commands termination of transcription on the 3'-end (e.g. a vector containing $rrnPT_1T_2$ is commercially available from Pharmacia), has an effect on protein synthesis efficiency in the recombinant.

Although commercially available products can be used as is for the vector that can be used for preparation of the recombinant vector of the present invention, various types of vectors induced according to a specific purpose can also be used. Examples of these include pBR322, pBR327, pKK223-3, pKK233-2 and pTrc99, originating in pMBl and having the replicon, pUC18, pUC19, pUC118, pUC119, pBluescript, pHSG298 and pHSG396, modified to improve the number of copies, pACYC177 and pACYC184, derived from p15A and having the replicon, as well as plasmids originating in pSC101, ColEl, RI and F factor. Moreover, expression vectors, for fused proteins, that are easier to purify, can also be used, examples of which include pGEX-2T, pGEX-3X and pMal-c2, and the example of a gene used as the starting material in the present invention is described in Japanese Patent Application No. 6-315572.

In addition, gene introduction can also be performed by using virus vectors and transposons such as λ-phages and M13 phages in addition to plasmids. In the case of gene introduction into a microorganism other than *E. coli*, gene introduction into Bacillus sp. is known using pUB110 (sold by Sigma) or pHY300PLK (sold by Takara Shuzo). These vectors are described in Molecular Cloning (J. Sambrook, E. F. Fritsch, T. Maniatis ed., Cold Spring Harbor Laboratory Press, pub.), Cloning Vector (P. H. Pouwels, B. E. Enger Valk, W. J. Brammar ed., Elsevier pub.) and various company catalogs.

Insertion of a DNA fragment coding for GGPP synthase and, as necessary, a DNA fragment having the function of regulating expression of the gene of the above-mentioned enzyme, into these vectors can be performed according to known methods using suitable restriction enzyme and ligase. Specific examples of plasmids of the invention prepared in this manner include pBS-GGPSmut1, PBS-GGPSmut2, pBS-GGPSmut3, pBS-GGPSmut4 and pBS-GGPSmut5.

Examples of microorganisms that can be used for gene introduction with this type of recombinant vector include E. coli and Bacillus sp. This transformation can also be performed according to routine methods such as the $CaCl_2$ method or protoplast method described in Molecular Cloning (J. Sambrook, E. F. Fritsch, T. Maniatis ed., Cold Spring Harbor Laboratory Press pub.) and DNA Cloning Vol. I-III (D. M. Glover ed., IRL Press pub.).

In producing the mutant enzyme of the present invention, the above-mentioned transformed cell is cultured after which the mutant enzyme can be collected and purified from that culture in accordance with routine methods, examples of which include salting out, organic solvent sedimentation, gel filtration, affinity chromatography, hydrophobic inter action chromatography and ion exchange chromatography.

In addition, the present invention provides a process for producing prenyl diphosphate using the enzyme of the present invention. In this process, the enzyme of the present invention should be allowed to react in a medium, and particularly an aqueous medium, and then the target prenyl diphosphate should be recovered from the reaction medium as desired. The enzyme may not only be purified enzyme, but also crude enzymes obtained by semi-purification through various stages, or a substance containing enzymes such as cultured microorganisms or the culture itself. In addition, the above-mentioned enzyme, crude enzyme or enzyme-containing substance may be an immobilized enzyme that has been immobilized in accordance with conventional methods.

Prenyl diphosphate having fewer carbon atoms than the target prenyl diphosphate, such as 5–20 carbon atoms and preferably less than 5 carbon atoms, and isopentyl diphosphate are used for the substrate. Water or an aqueous buffer, such as phosphate buffer, are used for the reaction medium.

EXAMPLES

The following Examples provide a more detailed explanation of the present invention. Furthermore, the materials used in the following Examples can all be easily acquired by a person with ordinary skill in the art as described below.

Strain C296-LH3 of the budding yeast, Saccharomyces cerevisiae (Tzagoloff, A. and Dieckmann, C. L. (1990) Microbiological Reviews 54, 211–255, Tzagoloff, A. et al. (1075) J. Sacteriol. 122, 826–831), was used for the screening host.

Plasmid pG3/Tl (Tzagoloff, A. and Dieckmann, C. L. (1990) Microbiological Reviews 54, 211–255, Tzagoloff A. et al. (1975) J. Bacteriol. 122, 826–831, Ashby, M. N. and Edwards, P. A. (1990) J. Biol. Chem. 265, 13157–13164) or plasmid YEpG3ΔSpH, from which portions other than the HexPS coding region had been removed from pG3/Tl (Ashby, M. N. and Edwards, P. A. (1990) J. Biol. Chem. 265, 13157–13164), was used for the positive control plasmid containing the HexPS gene.

Y-PGK, wherein the crtE gene portion had been removed from Y-crtE (Misawa, N. et al. (1990) J. Bacteriology 172, 6704–6712), was used for the expression vector for library preparation. Saccharomyces cerevisiae strain A451 was used as a wild strain used for the positive control.

However, the experimental materials required for the present invention are not limited to those described above, but rather completely similar substitutes can also be used.

Screening host mutant strain C2960-LH3 for screening is a deficient strain for the HexPS gene. In other words, a budding yeast HPS gene fragment can easily be obtained from a widely known wild strain of budding yeast by PCR using an already known budding yeast HexPS gene sequence (GenBank™/EMBL Data Bank accession number (s) J05547). If this gene fragment is then used by coupling with a yeast incorporating plasmid (Ylp) such as pRS403, pRS404, pRS405 or pRS406 (available from Stratagene), an HexPS-deficient strain can easily be created by widely conducted gene destruction using homologous recombination.

In addition, it also sufficient for the positive control plasmid if this gene fragment is inserted using a widely known budding yeast expression vector such as pYEUra3 (available from Clonetech) and pYES2 (available from Invitrogen). The strain used for the positive control is not limited to strain A451, but rather any strain is sufficient provided it retains the wild HexPS gene. In addition, it is sufficient to use a commercially available vector for the expression vector for library preparation such as pYEYra3 available from Clonetech or pYES2 available from Invitrogen.

LKC-18 reversed phase thin layer chromatography plates were purchased from Whatman Chemical Separation, Inc. $[1-^{14}C]IPP$ was purchased from Amersham.

Example 1
Plasmid Construction

New HindIII restriction enzyme sites were introduced both upstream and downstream of the GGPS gene (GenBank™/EMBL Data Bank accession number D28748) of Sulfolobus acidocaldarius by PCR using the chemically synthesized DNA primers 5'-AAGAGAAGCTTATGAGTTACTTTGAC-3'(SEQ ID NO: 7) and 5'-GATACCGCTTTATTTTCTCC-3'(SEQ ID NO: 8). Genomic DNA was purified in accordance with routine methods from Sulfolobus acidocaldarius, obtainable as ATCC33909 from the American Type Culture Collection (ATCC), and its clone DNA was then used for the template DNA of PCR.

The DNA fragment amplified with PCR was ligated to the HindIII site of plasmid pBluescript (KS$^+$) cleaved with HindIII to form pBS-GGPS. A crtE gene portion was removed by cleaving plasmid Y-crtE with HindIII, and the remaining portion containing the PGK promoter and PGK terminator was self-ligated to form Y-PGK. The insert portion containing GGPS gene obtained by severing pBS-GGPS with HindIII was introduced at the HindIII site of Y-PGK to form Y-GGPS.

Example 2
Random Mutagenesis of GGPS Gene

A random mutation was introduced into the region coding for GGPS gene using nitrite according to the method of Myers et al. (Myers, R. M. et al. (1985) Science 229, 242–247). Single strand DNA was isolated from E. coli containing pBS-GGPS by infection with helper phage M13K07, and this was then treated for 60 minutes with 1 M sodium nitrite. Next, the complementary strand was synthesized as primer using chemical synthesis DNA 5'-CCCCCCTCGAGGTCGACGGTATCGATAA-3' (SEQ ID NO: 9) corresponding to the sequence of the T7 promoter portion. The GGPS gene portion was then extracted with HindIII restriction enzyme, introduced at the HindIII site of Y-PGK, and transformed to E. coli strain XL1-Blue to prepare the library.

Example 3

Yeast Transformation and Screening

The budding yeast, Saccharomyces cerevisiae, was transformed by the spheroplast method according to the method of Ashby et al. (Ashby, M. N. and Edwards, P. A. (1990) J. Biol. Chem. 265, 13157–13164). Namely, HexPS-deficient strain C296-LH3 was transformed with the previously described plasmid library and cultured on leucine-deficient agar plate (leu⁻ plate) using the top agar method (3% bactoagar, 0.67% yeast nitrogen base, 0.05% yeast extract, 0.05% bacto peptone, 1.0 M sorbitol and 2% glucose).

The transformant having the Leu⁺ phenotype was inoculated onto YEPG (1% yeast extract, 2% ethanol, 2% bacto peptone and 3% glycerol), D (1% yeast extract, 2% ethanol, 2% bacto peptone, 3% glycerol and 0.1% glucose) and YPD (1% yeast extract, 2% bacto peptone and 2% glucose) agar media followed by incubation for 3 days at 30° C. Clones were selected from the C2960-LH3 transformants with plasmid containing mutated GGPS that grew on the YEPG agar plate, grew and formed colonies larger than those of non-transformed C296-LH3 on the D plate.

This complemented phenotype is considered to indicate that the electron transport chain is active during the respiration reaction, or in other words, that a active coenzyme Q was synthesized in the C296-LH3 cells. Five clones having this complemented phenotype were obtained from 1,400 transformants. As a result of retesting the resulting five clones, not only were they able to grow on YEPG agar plates, but they also possessed the ability to form colonies that were clearly larger than those of YEpG3ΔSpH/C296-LH3, having a plasmid that contains HexPS gene of yeast origin, on D agar plates. The plasmid DNA of these five clones were purified in accordance with routine methods.

These plasmids were named Y-GGPSmut1, Y-GGPSmut2, Y-GGPSmut3, Y-GGPSmut4 and Y-GGPSmut5.

Furthermore, since yeast strain C296-LH3 is deficient in HexPS activity, it is unable to biosynthesize coenzyme Q6 which has a hexaprenol group on its side chain. Since coenzyme Q6 is required for nonfermentative metabolism, C296-LH3 forms colonies on media containing a small amount of glucose that are smaller than those of the wild strain, and does not grow on media that only contains a non-fermentative substrate like glycerol for the carbon source. Prior to screening for mutated activity, the effects of expression in wild type ran GGPS derived from Sulfolobus acidocaldarius were investigated.

On the D plates, strain Y-GGPS/C296-LH3, which is strain C296-LH5 having a plasmid containing the wild type GGPS gene, was found to clearly form colonies smaller than those of YEpG3ΔSpH/C296-LH3 although intermediate to YEpG3ΔSpH/C296-LH3, possessing a plasmid containing HexPS gene of yeast origin, and C296-LH3, not possessing a plasmid. However, Y-GGPS/C296-LH3 was unable to grow on the YEPG plate. This screening method was therefore confirmed to be useful.

Example 4

Determination of DNA Nucleotide Sequence and its Analysis

The nucleotide sequences of DNA coding for the five mutant GGPS contained in the five types of purified plasmids were determined using the Perkin-Elmer Model 373A Fluorescent DNA Sequencer according to the dideoxy chain termination method. Analysis of the nucleotide sequences was performed using the genetic data analysis software, MacMollyTetra.

The amino acid substitution sites as deduced from the nucleotide sequence of each mutant GGPS are shown in FIG. 1. Replacement sites were found at the nucleotide sequence level for all selected mutants. In the case of Mutant 1 which is the Y-GGPSmut1 insertion fragment, replacements were found consisting of mutant methionine at position 85 changing to isoleucine, mutant arginine at position 199 changing to lysine, and mutant aspartic acid at position 312 changing to asparagine. In the case of Mutant 2 which is the Y-GGPSmut2 insertion fragment, the only replacement was mutant phenylalanine at position 118 changing to leucine. In the case of Mutant 3 which is the Y-GGPSmut3 insertion fragment, mutant Phe at position 77 changed to serine, in the case of Mutant 4 which is the Y-GGPSmut4 insertion fragment, mutant phenylalanine at position 77 changed to leucine and mutant valine at position 99 changed to methionine, and in the case of Mutant 5 which is the Y-GGPSmut5 insertion fragment, mutant phenylalanine at position 77 changed to serine and mutant tyrosine at position 101 changed to histidine.

A high proportion of these mutations consist of an aromatic amino acid residue being replaced with a non-aromatic amino acid residue. Phenylalanine at position 77 in particular has the most significant effect on the chain elongation reaction. Phenylalanine at position 77 is located at the five residues upstream from the N-terminal residue of an aspartate-rich domain I. There are two aspartate-rich domain motifs (DDXX(XX)D) that are conserved in prenyl transferase. The diphosphate portion of the substrates are believed to bind here. The amino acid residue located at the fifth position upstream from the U-terminal residue of this aspartate-rich domain, which was focused on for the first time in the present invention, is considered to be extremely important in determining the chain length of the reaction product.

Example 5

A crude extract was prepared from the five selected clones (Y-GGPSmut1/C296-LH3, Y-GGPSmut2/C296-LH3, Y-GGPSmut3/C296-LH3, YGGPSmut4/C296-LH3 and Y-GGPSmut5/C-296-LH3) according to the method of Itoh et al. (Itoh, N. et al. (1984) J. Biol. Chem. 259, 13923–13929).

Namely, the above-mentioned yeast was incubated for 4 days at 30° C. Approximately 400 μg of cells were collected by centrifugation and washed once with 800 μl of buffer A (50 mM Tris.HCl pH 7.5, 5 mM MgCl₂, 50 mM dithiothreitol, 1M sorbitol). The cells were then suspended in 1.2 mM buffer B (50 mM Tris.HCl pH 7.5, 5 mM MgCl₂, 3 mM dithiothreitol, 1M sorbitol) followed by the addition of 0.8 mg of zymolyase and incubation for 1 hour at 30° C.

The prepared spheroblasts were washed three times with buffer B and suspended in 1 ml of buffer C (50 mM Tris.HCl pH 7.0, 10 mM 2-mercaptoethanol, 1 mM phenylmnethane-sulfonyl fluoride, 1 mM EDTA). Ultrasonic treatment was performed 10 times on the suspension in ice at two minute intervals, performing treatment for 10 seconds at a time at maximum output using a Branson Sonifier. The lysates were incubated for 1 hour at 55° C., and after inactivating prenyl transferase(s) of the host cells, the lysates were centrifuged for 10 minutes at 10,000×g. The resulting supernatant was used as a mutant GGPS crude enzyme solution and assay of prenyl transferase activity.

Figure 2:
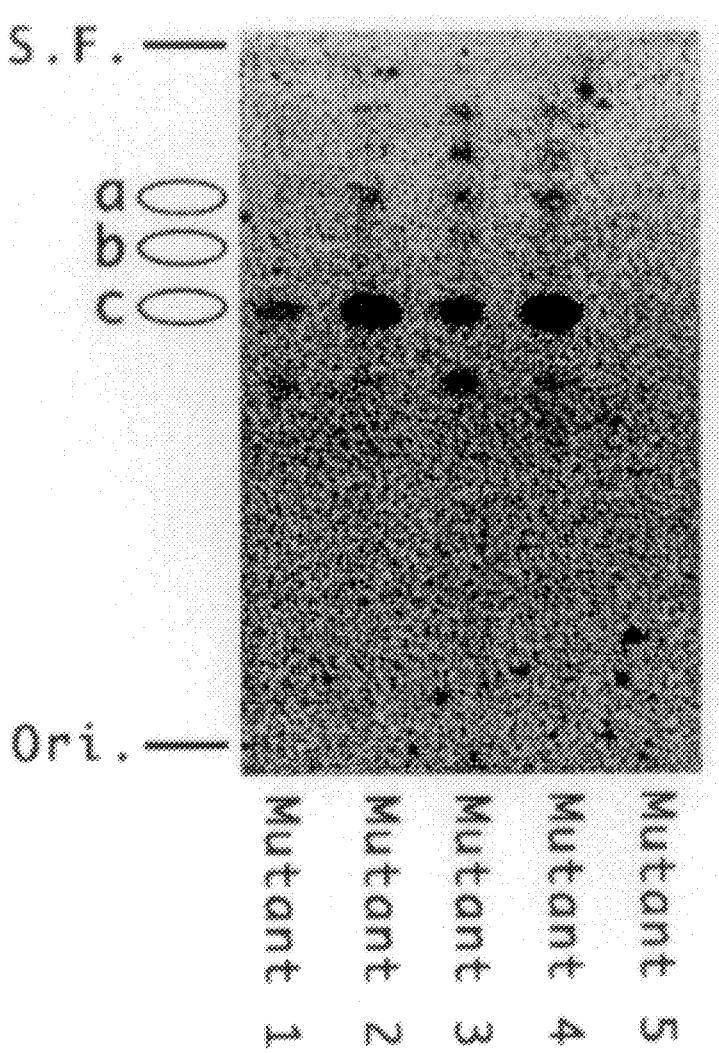
FIG. 2 is photograph that indicates the autoradiograph of a thin layer chromatography which shows the products in the case of allowing the mutant enzymes of the present invention produced in yeast to act on substrates IPP and (all-E)-FPP. The ellipses show the positions of cold authentic samples, which are geraniol, farnesyl, and geranilgeranil for a, b and c respectively.
Figure 3:
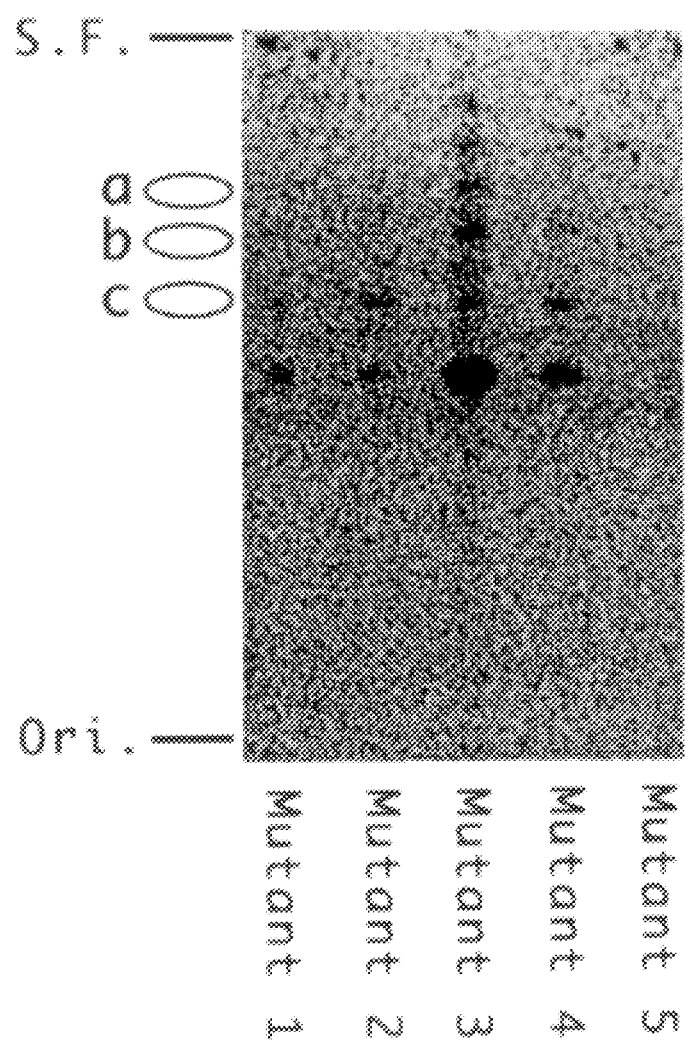
FIG. 3 is a photograph that indicates the autoradiograph of a thin layer chromatography which shows the products in the case of allowing the mutant enzyme of the present invention produced in yeast to act on substrates IPP and (all-E)-GGPP. The ellipses show the positions of cold authentic samples, which are geraniol, farnesyl, and geranilgeranil for a, b and c respectively.

The results of performing an assay of prenyl transferase activity by LKC-18 thin layer chromatography using this mutant GGPS crude enzyme liquid prepared from yeast are shown in FIGS. 2 and 3.

After carrying out the enzyme reaction at 55° C., polyprenyl diphosphate was extracted with 1-butanol after which the 1-butanol was evaporated with a nitrogen gas flow. The resulting polyprenyl diphosphate was treated with acid phosphatase in accordance with the method of Fujii et al. (Fujii et al. (1982) Biochim. Biophys. Acta. 712, 716–718). The hydrolysis product was extracted with pentane and after performing thin layer chromatography using acetone/$H_2O$ (9:1) for the developing solution, the distribution of radioactivity was analyzed with the Fuji Film Model BAS2000 Bio-image Analyzer. The alcohols as the authentic standards, on which thin layer chromatography was performed simultaneously, followed by staining with iodine vapor (geranyol, farnesol, geranylgeraniol), were used to determine the developing locations.

FIG. 2 shows the result of reacting using [1-$^{14}$C]IPP and (all-E)-FPP for the substrates, while FIG. 3 shows the result of reacting using [1-$^{14}$C]IPP and (all-E)-GGPP for the substrates. Spots a through c correspond to the authentic standard samples, a indicating geraniol, b indicating (all-E) -farnesol, and c indicating (all-E)-geranylgeranyol. Ori indicates the sample-stopping point, S.F. indicates the solvent front.

On the basis of these results, in the case of using GGPP for the allylic substrate, it was shown that each mutant GGPS is able to synthesize geranylfarnesyl diphosphate (GFPP) that is one isoprene unit longer than the reaction product of the wild type enzyme. On the other hand, the wild type GGPS is unable to synthesize the reaction product same as or longer than the chain length of GFPP at a level that allows detection. In the case of using FPP for the allylic substrate, the product ratio of GGPP/GFPP indicated by the mutant GGPS was different from each other.

Example 6
Preparation of Mutant GGPS from E. coli

In order to ensure that the analysis is performed more accurately, each mutant GGPS was over expressed in E. coli strain of XL 1-Blue. Namely, each of the five plasmids Y-GGPSmut1, Y-GGPSmut2, Y-GGPSmut3, Y-GGPSmut4 and Y-GGPSmut5 obtained in screening was digested with HindIII to obtain HindIII DNA fragments that code for the mutant GGPS. These HindIII DNA fragments were inserted at the HindIII site of the plasmid vector pBluescript (KS($^+$)) to obtain pBS-GGPSmut1, pBS-GGPSmut2, pBS-GGPSmut3, pBS-GGPSmut4 and pBS-GGPSmut5 respectively.

E. coli XL1-Blue was transformed with pBS-GGPSmut1, pBS-GGPSmut2, pBS-GGPSmut3, pBS-GGPSmut4 and pBS-GGPSmut5 and cultured according to the method described in Molecular Cloning (Sambrook, J. et al. (1189) Molecular Cloning: A Laboratory Manual, 2nd Ed., Cold Spring Harbor Laboratory, Cold Spring Harbor, N.Y.). After collecting the bacterial cells, the bacterial cells were ultrasonically homogenized in 50 mM Tris.HCl buffer containing 10 mM 2-mercaptoethanol and 1 mM EDTA. After heat treating the homogenate for 1 hour at 55° C., it was centrifuged for 10 minutes at 100,000×g. The supernatant was then collected as the crude enzyme solution which was assayed for PTase activity.

Figure 4:
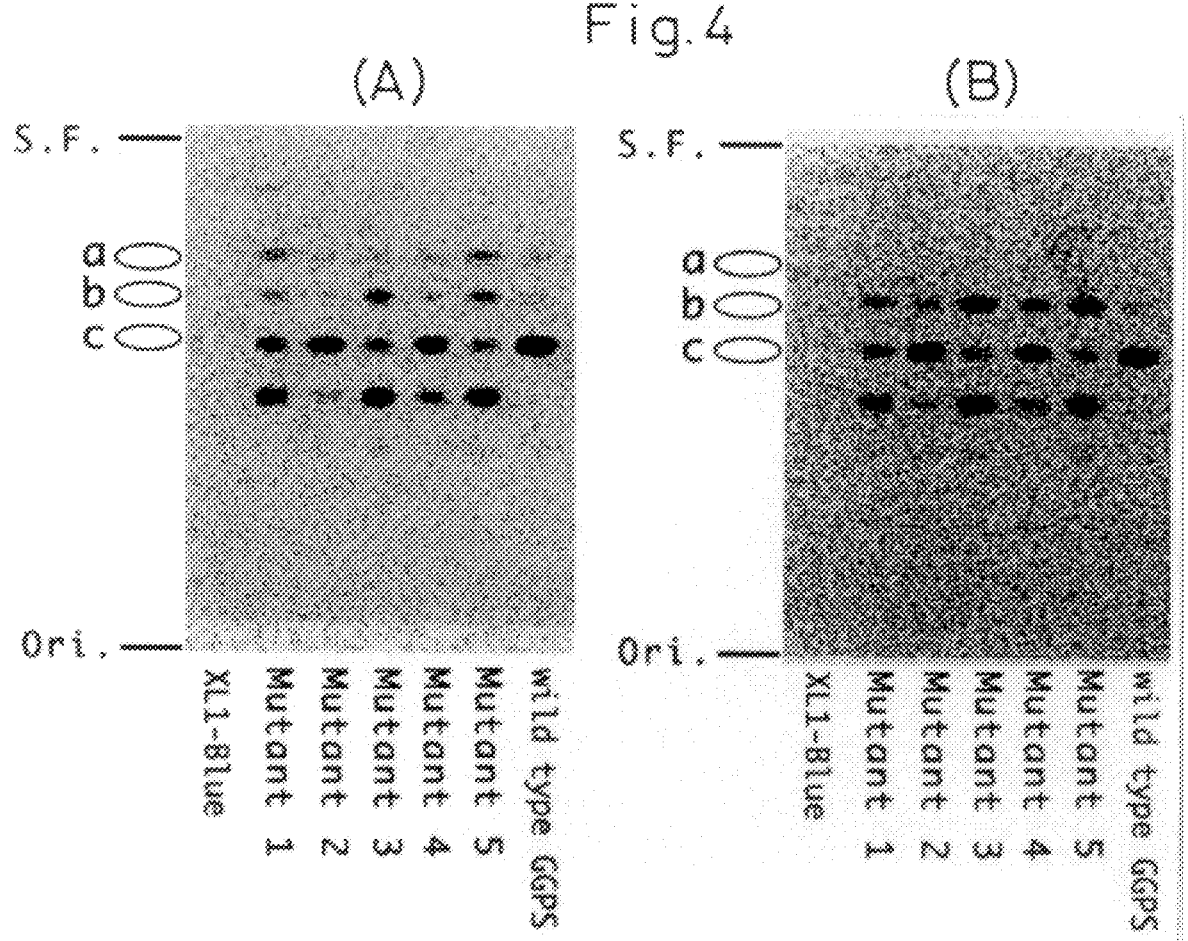
FIG. 4 is a photograph that indicates the autoradiograph of a thin layer chromatography which shows the products in the case of allowing the mutant enzyme of the present invention produced in E. coli to act on (A) substrates IPP and DMAPP, and on (B) substrates IPP and GPP. The ellipses show the positions of cold authentic samples, which are geraniol, farnesyl, and geranilgeranil for a, b and c respectively.
Figure 5:
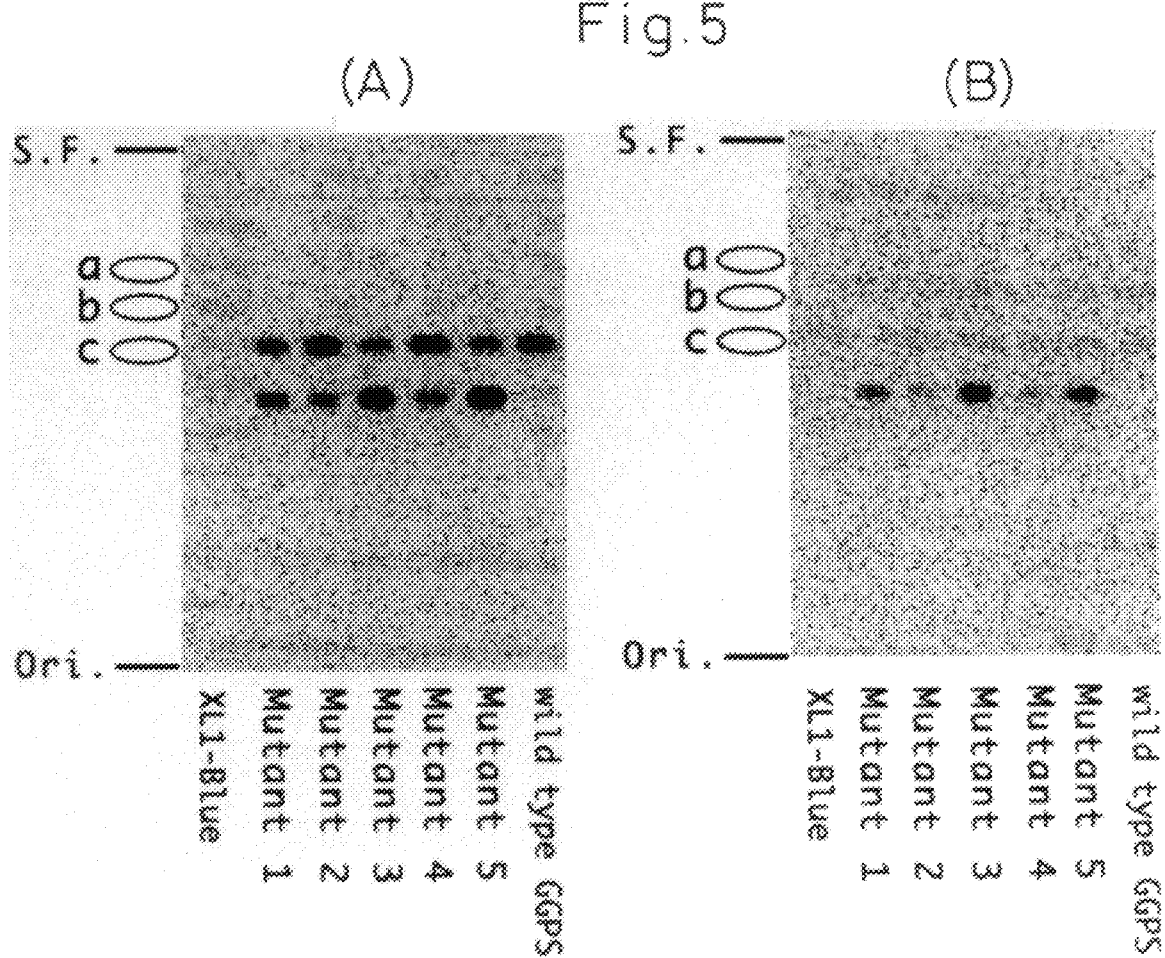
FIG. 5 is the autoradiograph of a photograph that indicates a thin layer chromatography which shows the products in the case of allowing the mutant enzyme of the present invention produced in E. coli to act on (A) substrates IPP and (all-E)-FPP, and Dn (B) substrates IPP and (all-E)-GGPP. The ellipses show the positions of cold authentic samples, which are geraniol, farnesyl, and geranilgeranil for a, b and c respectively.

Assay was performed by analysis of product with LKC-18 thin layer chromatography and by determination of enzyme activity. For thin layer chromatography, DMAPP, GPP, (all-E)-FPP and (all-E)-GGPP were used for the allylic substrates, and after reacting in the same manner as Example 5,LKC thin layer chromatography was performed in the same manner as Example 5. Those results are shown in FIGS. 4 and 5.

FIG. 4(A) is the result of reacting [1-$^{14}$C]IPP with DMAPP for the substrate, and (B) is the result of reacting [1-$^{14}$C]IPP with GPP for the substrate. FIG. 5(C) is a result of reacting [1-$^{14}$C]IPP with (all-E)-FPP for the substrate, while (D) is a result of reacting [1-$^{14}$C]IPP with (all-E)-GGP for the substrate. Ellipses a through c show the positions of the authentic standard samples, a indicating geraniol, b indicating (all-E)-farnesol and c indicating (all-E)-geranylgeraniol. Ori indicates the sample-spoting point, while S.F. indicates the solvent front.

The prenyl transferase activity was assaied as follows. 1 ml of assay mixture, containing 25 nmol of [1-$^{14}$C]IPP (37 GBq/mol), 25 nmol of allylic substrate (DMAPP, GPP, (all-E)-FPP or (all-E)-GGPP), 5 μmol of $MgCl_2$, 10 μmol of phosphate buffer (pI 5.8) and the enzyme solution, was incubated for 60 minutes at 55° C.

The reaction was stopped by cooling rapidly on ice. After adding 3–5 ml of water-saturated 1-butanol to the chilled mixture and shaking vigorously, the 1-butanol layer was washed with NaCl-saturated water and $^{14}$C radioactivity was measured with a liquid scintillation counter. 1 unit of enzyme activity was defined as the amount for which 1 nmol of [1-$^{14}$C]IPP is incorporated into elongated prenyl-diphosphate (polyprenyl diphosphate) that can be extracted with the 1-butanol layer. Those results are shown in the Table,

TABLE

| Substrate | Relative Activity (dpm) | Product Distribution | | | | |
|---|---|---|---|---|---|---|
| | | GPP % | FPP % | GGPP % | GFPP % | FFPP % |
| Mutant 1 | | | | | | |
| DMAPP | 31,800 | 23.2 | 8.77 | 29.6 | 38.0 | 0.45 |
| GPP | 5,260 | nd* | 38.8 | 30.9 | 30.4 | 0.02 |
| FPP | 4,340 | nd* | nd* | 65.1 | 35.0 | nd* |
| GGPP | 998 | nd* | nd* | nd* | 100 | nd* |
| Mutant 2 | | | | | | |
| DMAPP | 15,800 | 1.44 | 0.66 | 89.0 | 8.86 | nd* |
| GPP | 7,050 | nd* | 20.3 | 74.9 | 4.89 | nd* |
| FPP | 6,080 | nd* | nd* | 89.5 | 10.5 | nd* |
| GGPP | 379 | nd* | nd* | nd* | 100 | nd* |
| Mutant 3 | | | | | | |
| DMAPP | 24,900 | 3.40 | 27.4 | 16.6 | 51.6 | 0.92 |
| GPP | 9,890 | nd* | 64.7 | 9.37 | 24.5 | 1.44 |
| FPP | 7,280 | nd* | nd* | 30.4 | 69.6 | nd* |
| GGPP | 3,200 | nd* | nd* | nd* | 100 | nd* |
| Mutant 4 | | | | | | |
| DMAPP | 16,700 | 4.93 | 4.07 | 73.2 | 17.8 | nd* |
| GPP | 7,460 | nd* | 38.4 | 51.3 | 10.3 | nd* |
| FPP | 5,650 | nd* | nd* | 85.9 | 14.1 | nd* |
| GGPP | 551 | nd* | nd* | nd* | 100 | nd* |
| Mutant 5 | | | | | | |
| DMAPP | 23,600 | 27.1 | 18.6 | 12.8 | 40.4 | 1.12 |

TABLE-continued

| Sub-strate | Relative Activity (dpm) | GPP % | FPP % | GGPP % | GFPP % | FFPP % |
|---|---|---|---|---|---|---|
| GPP | 9,070 | nd* | 59.3 | 13.0 | 26.1 | 1.56 |
| FPP | 8,960 | nd* | nd* | 32.0 | 68.0 | nd* |
| GGPP | 2,200 | nd* | nd* | nd* | 100 | nd* |
| Wild type | | | | | | |
| DMAPP | 13,600 | 5.61 | 0.43 | 94.0 | nd* | nd* |
| GPP | 6,640 | nd* | 17.2 | 82.8 | nd* | nd* |
| FPP | 4,650 | nd* | nd* | 100 | nd* | nd* |
| GGPP | nd* | nd* | nd* | nd* | nd* | nd* | nd: Not detected

Each mutant GGPS exhibited activity that synthesizes polyprenyl diphosphate having a longer chain length than GGPP, The wild type GGPS as well as each mutant GGPS reacted the best with DMAPP amongst the four allylic substrates. In addition, relative activity when allylic substrates were used that had a shorter chain length than FPP exhibited similar values. However, relative activity and product distribution when GGPP was used for the allylic substrate were considerably different.

When DMAPP, GPP and FPP were used for the allylic substrates, Mutant 1, which is coded for by the insert DNA of plasmid pBS-GGPSmut1, yielded the major reaction products of GFPP and GGPP. In particular, when DMAPP was used for the allylic substrate, only a slight amount of hexaprenyl diphosphate (HexPP) was detected as the reaction product. Although the distribution of reaction products varied between each allylic substrate, the proportion of product produced in one cycle of the condensation reaction was large.

In the case of Mutant 2 coded for by the insert DNA of plasmid pBS-GGPSmut2, the major product was GGPP and the proportion of GFPP was roughly 10%. HexPP was not detected.

Mutant 3, which is coded for by the insert DNA of plasmid pBS-GGPSmut3, and Mutant 5, which is coded for by the insert DNA of plasmid pBS-GGPSmut5, demonstrated similar characteristics. These mutants exhibited strong GFPP synthesis activity, while also synthesizing a small amount of HexPP.

Mutant 4, which is coded for by the insert DNA of plasmid pBS-GGPSmut4, yielded GGPP as the major product, while the proportion of GFPP was roughly 15%. FPP was effectively synthesized when GPP was used for the allylic substrate.

We claim:

1. A gene that codes for a mutated *Sulfolobus acidocaldarius* geranylgeranyl diphosphate synthase selected from the group consisting of:

Mutant 1, having isoleucine at amino acid position 85, lysine at amino acid position 199 is replaced with lysine, and asparagine at amino acid position 312;

Mutant 2, having leucine at amino acid position 118;

Mutant 3, having serine at amino acid position 77;

Mutant 4, having leucine at amino acid position 77 and methionine at amino acid position 99; and Mutant 5, having serine at amino acid position 77 and histidine at amino acid position 101 wherein the wild-type enzymer is encoded by SEQ ID NO:1, and;

wherein said mutated enzyme forms prenyl diphosphate having at least 25 carbon atoms.

2. An expression vector that contains a gene as set forth in claim 1.

3. A host transfected by an expression vector as set for in claim 2.

4. A process for the production of an enzyme as set forth in claim 1 comprising the steps of:

culturing in medium host cells transformed with an expression vector comprising a gene coding for mutated geranylgeranyl diphosphate synthase, and recovering said mutated geranylgeranyl diphosphate synthase from the medium.

5. A process for production of a mutated prenyl diphosphate synthase comprising the step of:

transforming a host cell with a gene encoding a mutant prenyl diphosphate synthase, said gene containing a nucleotide codon encoding a non-aromatic amino acid residue located at position five amino acids upstream of the amino terminal end of the aspartic acid-rich domain 1 of prenyl diphosphate synthase, wherein the wild-type prenyl diphosphate synthase is encoded by SEQ ID NO:1.

\* \* \* \* \*